(12) United States Patent
Jiang et al.

(10) Patent No.: US 9,055,977 B2
(45) Date of Patent: Jun. 16, 2015

(54) POROUS METAL DEVICE FOR REGENERATING SOFT TISSUE-TO-BONE INTERFACE

(71) Applicant: Zimmer, Inc., Warsaw, IN (US)

(72) Inventors: Tao Jiang, Austin, TX (US); Jian Q. Yao, Shanghai (CN); Hali Wang, The Hills, TX (US); Timothy A. Hoeman, Morris Plains, NJ (US); Ray Zubok, Midland Park, NJ (US); John Chernosky, Brick, NJ (US); Keith A. Roby, Jersey City, NJ (US)

(73) Assignee: Zimmer, Inc., Warsaw, IN (US)

( * ) Notice: Subject to any disclaimer, the term of this patent is extended or adjusted under 35 U.S.C. 154(b) by 67 days.

(21) Appl. No.: 13/679,041

(22) Filed: Nov. 16, 2012

(65) Prior Publication Data

US 2013/0131699 A1    May 23, 2013

Related U.S. Application Data

(60) Provisional application No. 61/561,475, filed on Nov. 18, 2011, provisional application No. 61/699,373, filed on Sep. 11, 2012.

(51) Int. Cl.
*A61F 2/08* (2006.01)
*A61B 17/68* (2006.01)
(Continued)

(52) U.S. Cl.
CPC .............. *A61B 17/68* (2013.01); *A61L 27/56* (2013.01); *A61F 2/0811* (2013.01);
(Continued)

(58) Field of Classification Search
CPC ............. A61F 2/08; A61F 2/28; A61L 27/00; A61B 17/68

USPC .............. 606/62–64, 151, 232, 286–289, 606/300–323; 623/13.11–13.14, 623/23.47–23.63

See application file for complete search history.

(56) References Cited

U.S. PATENT DOCUMENTS

| 5,282,861 A | 2/1994 | Kaplan |
| 2005/0112397 A1 | 5/2005 | Rolfe et al. |

(Continued)

FOREIGN PATENT DOCUMENTS

| WO | WO-2009154781 A1 | 12/2009 |
| WO | WO-2010017959 A2 | 2/2010 |
| WO | WO-2013074909 A1 | 5/2013 |

OTHER PUBLICATIONS

"International Application Serial No. PCT/US2012/065491, International Search Report mailed Feb. 11, 2013", 5 pgs.

(Continued)

*Primary Examiner* — Yashita Sharma
(74) *Attorney, Agent, or Firm* — Schwegman Lundberg & Woessner, P.A.

(57) ABSTRACT

The present disclosure relates, in some aspects, to orthopaedic implants for securing soft tissue to bone and methods for using the same. One particular implant comprises a first exposed porous surface region, having pores for promoting bone ingrowth, and a second exposed porous surface, having pores for promoting soft tissue ingrowth. At least some of the pores of the first exposed porous surface region may be seeded with osteocytic factors and at least some of the pores of the second exposed porous surface region may be seeded with fibrocytic factors. Such orthopaedic implants can advantageously facilitate regeneration of the soft tissue to bone interface.

27 Claims, 14 Drawing Sheets

(51) Int. Cl.
*A61B 17/08* (2006.01)
*A61L 27/56* (2006.01)
*A61L 27/04* (2006.01)

(52) U.S. Cl.
CPC  *A61F 2002/0858* (2013.01); *A61F 2002/0888* (2013.01); *A61F 2250/0021* (2013.01); *A61F 2250/0023* (2013.01); *A61F 2250/0026* (2013.01); *A61L 27/04* (2013.01)

(56) References Cited

U.S. PATENT DOCUMENTS

2005/0159812 A1     7/2005  Dinger, III et al.
2005/0246032 A1*   11/2005  Bokros et al. ................ 623/23.6
2007/0162022 A1     7/2007  Zhang et al.

OTHER PUBLICATIONS

"International Application Serial No. PCT/US2012/065491, Written Opinion mailed Feb. 11, 2013", 6 pgs.
Bobyn, J. D., et al., "Characterization of new porous tantalum biomaterial for reconstructive orthopaedics", Scientific Exhibition: 66th Annual Meeting of the American Academy of Orthopaedic Surgeons, Feb. 4-8, 1999; Anaheim, CA, (1999), 1 pg.
Levine, Brett R, et al., "Experimental and clinical performance of porous tantalum in orthopedic surgery", Biomaterials, 27(27), (Sep. 2006). 4671-81.
Zhang, Y., et al., "Interfacial frictional behavior: Cancellous bone, cortical bone, and a novel porous tantalum biomaterial". Journal of Musculoskeletal Research, 3(4), (1999), 245-251.
"International Application Serial No. PCT/US2012/065491, International Preliminary Report on Patentability mailed May 30, 2014", 8 pgs.

* cited by examiner

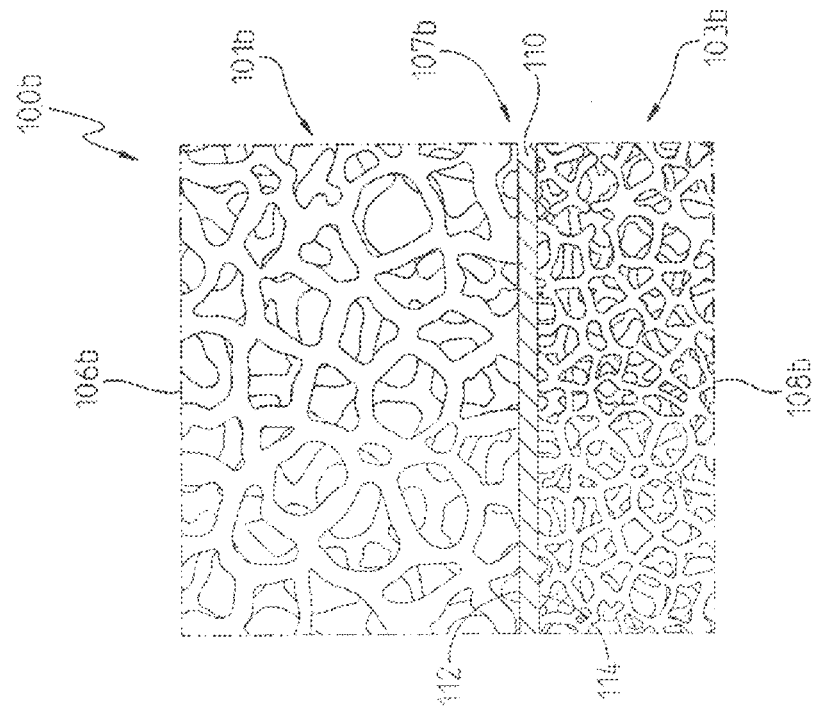
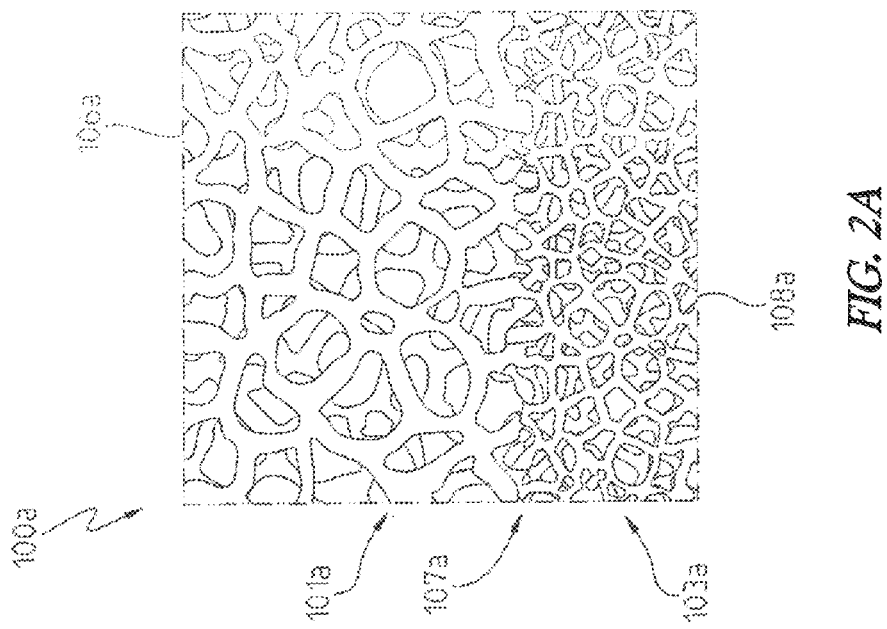
FIG. 2A
FIG. 2B

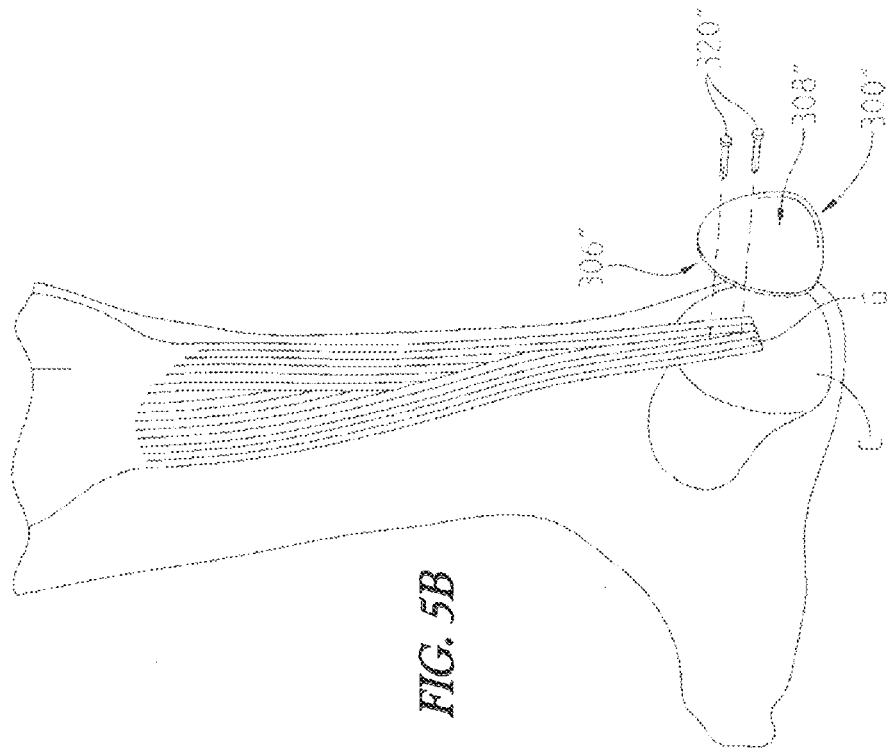
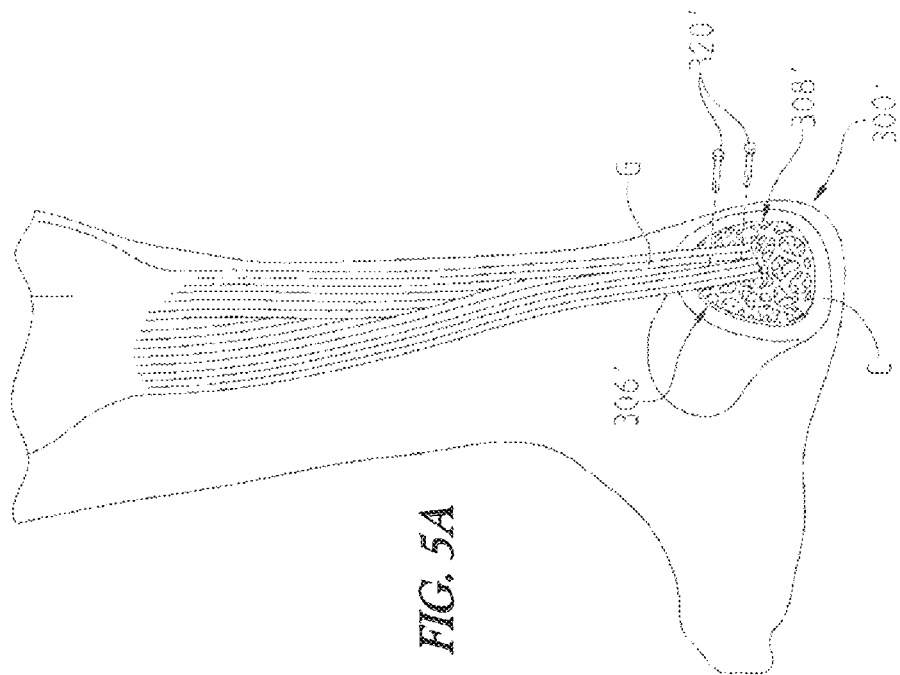

POROUS METAL DEVICE FOR REGENERATING SOFT TISSUE-TO-BONE INTERFACE

CLAIM OF PRIORITY

This application claims the benefit of priority under 35 U.S.C. §119(e) of Jiang et al., U.S. Provisional Patent Application Ser. No. 61/561,475, entitled "POROUS METAL DEVICE FOR REGENERATING SOFT TISSUE-TO-BONE INTERFACE", filed on Nov. 18, 2011, and also claims the benefit of priority under 35 U.S.C. §119(e) of Hoeman et al., U.S. Provisional Patent Application Ser. No. 61/699,373, entitled "POROUS METAL DEVICE FOR REGENERATING SOFT TISSUE-TO-BONE INTERFACE", filed on Sep. 11, 2012, which are herein incorporated by reference in its respective entirety.

BACKGROUND

1. Field of the Disclosure

The present disclosure relates to orthopaedic implants. More particularly, some aspects of the present disclosure relate to orthopaedic implants including an exposed open porous metal surface for securing soft tissue to bone.

2. Description of the Related Art

Soft tissue injuries, such as tendon and ligament tears, are common following traumatic injury or due to deterioration of joints. Repair of tendon and ligament injuries commonly requires surgical intervention. In some cases, a surgeon will suture the torn ligament or tendon to bone. In other instances, a graft may be required to reconnect the tendon or ligament to bone. Even after surgically repairing tendon and ligament injuries, optimal function of a joint may not fully be restored. In such cases, revision surgical procedures are commonly required.

Problems associated with current treatment methods for tendon and ligament injuries include an inability to provide adequate initial stiffness and strength of the repaired tendon or ligament, as well as an inability regenerate the bone to soft tissue interface. The interface at which the ligament or tendon contacts bone represents a potential mechanical weak point of a repaired tendon or ligament. Thus, regeneration of the bone to soft tissue interface may enhance the success rate of surgical repair of tendon and ligament injuries.

SUMMARY

Some aspects of the present disclosure relate to an orthopaedic implant and method of utilizing the same for securing soft tissue to bone. The orthopaedic implants and methods of the present disclosure can be useful, for example, to repair ligament injuries, such as anterior cruciate ligament tears, and tendon injuries, such as rotator cuff and Achilles tendon tears. Moreover, some of the orthopaedic implants and methods disclosed herein promote soft tissue and bone ingrowth within the orthopaedic implants, thereby facilitating regeneration of the soft tissue to bone interface.

According to one embodiment of the present disclosure, an orthopaedic implant for securing soft tissue to bone is presented which includes an open porous metal body having an exterior that includes an exposed porous metal exterior surface suitable for contacting bone. Additionally, the body includes an opening in the exterior of the body that provides access to an exposed porous interior surface suitable for contacting soft tissue. In some forms, the body will incorporate a cannula or passage for receiving soft tissue such as where the body is a fully cannulated tube, e.g., a cylindrical tube.

According to another embodiment of the present disclosure, an orthopaedic implant for securing soft tissue to bone is presented including an open porous metal hollow body having an exposed porous interior surface for contacting soft tissue. The open porous metal hollow body of the orthopaedic implant also includes an exposed porous exterior surface for contacting bone and a first opening dimensioned for receiving a first end of a soft tissue graft. The open porous metal hollow body is also fully cannulated. In some configurations of the orthopaedic implant, the open porous metal hollow body is substantially cylindrical in shape. In other configurations, however, the open porous metal hollow body has a cross section selected from one of a circle, semi-circle, ellipse, oval or other arcuate shape. In yet other configurations of the orthopaedic implant, the open porous metal hollow body has a cross section selected from one of a triangle, square, rectangle or other polygon with four or more sides. Additionally, configurations of the orthopaedic implant may include the interior surface having a first coefficient of friction and the exterior surface having a second coefficient of friction which is different than the first coefficient of friction.

According to another embodiment of the present disclosure, an implant for securing soft tissue to bone is presented comprising a monolithic open porous metal body, e.g., in the form of a sheet or tube. The monolithic open porous metal body comprises a first soft tissue attachment layer having a plurality of pores with a first nominal pore diameter and the first layer has a thickness, e.g., of between one and six pore diameters, or between two and ten pore diameters, or between five and twenty pore diameters, or less than thirty pore diameters, or having any suitable thickness. The monolithic open porous metal also comprises a second bone attachment layer having a plurality of pores with a second nominal pore diameter and the second layer also has a thickness, e.g., of between one and six pore diameters, or between two and ten pore diameters, or between five and twenty pore diameters, or less than thirty pore diameters, or having any suitable thickness. In certain forms, at least one of the first layer and second layer can include at least one fibrocytic factor or osteocytic factor. In some configurations of the orthopaedic implant, the pores of the first layer are seeded with a fibrocytic factor. Additionally, in some configurations, the pores of the second layer are seeded with an osteocytic factor. Further, some configurations of the orthopaedic implant include the first nominal pore diameter being less than the second nominal pore diameter.

According to yet another embodiment of the present disclosure, an implant for securing soft tissue to bone is provided, comprising a monolithic open porous metal body. The monolithic open porous metal body includes a soft tissue securing portion and a bone anchoring portion. In some configurations of the orthopaedic implant, the bone anchoring portion includes a screw thread and the soft tissue securing portion includes an eyelet with a passage therethrough. Further, according to this configuration of orthopaedic implant, the fixation means has an outer surface with a first coefficient of friction and the passage has an inner surface with a second coefficient of friction which is less than the first coefficient of friction.

In another embodiment, the present disclosure provides an implant for securing soft tissue to bone. This particular implant comprises a tubular body that provides an inner passageway for receiving soft tissue of a patient. The inner passageway includes an interior side wall that is provided by a first open porous metal structure with pores of a first nominal pore diameter for suitably receiving soft tissue ingrowth. The tubular body includes an exterior side wall that is provided by a second open porous metal structure with pores of a second nominal pore diameter greater than the first nominal pore diameter for suitably receiving bone ingrowth. The inner passageway may or may not extend entirely through the tubular body. The inner passageway may or may not pass through the second open porous metal structure. The first open porous metal structure may or may not be tubular. When tubular, the first open porous metal structure can have any suitable shape, e.g., having a section with a circular or non-circular cross section. When the first open porous metal structure is tubular, the second open porous metal structure may or may not be tubular. In some forms, the second also will be tubular and will be positioned substantially concentrically around the tubular first open porous metal structure. In some other forms, the second open porous metal structure will be non-tubular (e.g., a sheet or layer with or without curvature) and will be positioned laterally adjacent the tubular first open porous metal structure. In some embodiments, the tubular body will include a side wall thickness that extends between the interior side wall of the inner passageway and the exterior side wall of the tubular body, and this thickness will be provided entirely by open porous metal.

BRIEF DESCRIPTION OF THE DRAWINGS

The above-mentioned and other features and advantages of this disclosure, and the manner of attaining them, will become more apparent and the disclosure itself will be better understood by reference to the following description of embodiments of the disclosure taken in conjunction with the accompanying drawings, wherein:

FIG. 2a is a cross-sectional view of an embodiment of open porous metal having larger pore sizes proximate the first exposed porous surface region and smaller pore sizes proximate the second exposed porous surface region;

FIG. 2b is another cross-sectional view of an embodiment of open porous metal having larger pore sizes proximate the first exposed porous surface region and smaller pore sizes proximate the second exposed porous surface region with an interface substrate separating the plurality of pores proximate the first exposed porous surface region from the plurality of pores proximate the second exposed porous surface region;

FIG. 5a is a perspective view illustrating an Achilles tendon secured to a bone in the ankle with an orthopaedic implant according to the present disclosure;

FIG. 5b is a perspective view illustrating an Achilles tendon secured to a bone in the ankle with another embodiment of an orthopaedic implant according to the present disclosure;

FIG. 12b is a top view of the orthopaedic implant shown in FIG. 12a.

Corresponding reference characters indicate corresponding parts throughout the several views. The exemplifications set out herein illustrate exemplary embodiments of the disclosure and such exemplifications are not to be construed as limiting the scope of the disclosure in any manner.

DETAILED DESCRIPTION

Introduction

Some aspects of the present disclosure generally relate to orthopaedic implants for securing soft tissue to bone and methods of utilizing the orthopaedic implants disclosed herein. In some embodiments, the orthopaedic implants disclosed herein comprise an open porous metal which defines an exposed porous surface particularly suited for contacting bone, and an exposed porous surface particularly suited for contacting soft tissue. Advantageously, these orthopaedic implants and some of the methods disclosed herein can be used to promote the regeneration of the soft tissue to bone interface.

Open Porous Metal.

Figure 1:
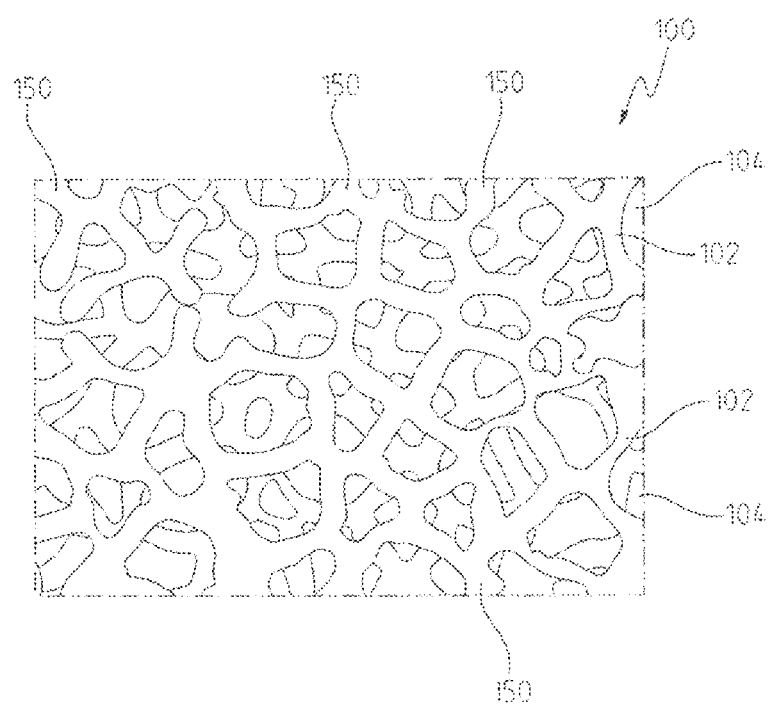
FIG. 1 is an enlarged view of the structure of open porous metal according to the instant disclosure.

The orthopaedic implants disclosed herein are comprised of open porous metal 100, shown in FIG. 1. According to some embodiments of the orthopaedic implants disclosed herein, open porous metal 100 may comprise all or a substantial portion of the implant. Additionally, open porous metal 100 comprises exposed porous metal surfaces of the orthopaedic implants which, as described herein, are particularly suited for contacting bone and soft tissue.

Referring to FIG. 1, an illustrative embodiment of open porous metal 100 is depicted. As shown, open porous metal 100 generally includes a large plurality of ligaments 102 defining open voids (i.e., pores) or channels 104 therebetween. The open voids between ligaments 102 form a matrix of continuous channels 104 having few or no dead ends, such that growth of soft tissue and/or bone through open porous metal 100 is substantially uninhibited. Open porous metal 100 may include up to 75%-85% or more void space therein. Thus, open porous metal 100 may comprise a lightweight, strong porous structure which is substantially uniform and consistent in composition, and provides a matrix into which soft tissue and bone may grow to regenerate and strengthen anchoring of soft tissue to bone at the soft tissue to bone interface.

According to some configurations of the instant disclosure, the exposed porous metal surfaces of the orthopaedic implants disclosed herein comprise open porous metal 100. For example, with reference to FIGS. 2a and 2b, first surface 106 and second surface 108 of open porous metal 100 may comprise the exposed porous metal surfaces of the orthopaedic implants disclosed herein. As depicted, the terminating ends of ligaments 102 (comprising open porous metal 100), referred to herein as struts 150, define first surface 106 and second surface 108. Struts 150 generate a high coefficient of friction along first surface 106 and second surface 108 (comprising the exposed porous metal surfaces of open porous metal 100). Further, struts 150 impart an enhanced affixation ability to the exposed porous metal surfaces of open porous metal 100 for adhering to bone and soft tissue.

Open porous metal 100 may be made of a highly porous biomaterial useful as a bone substitute and/or cell and tissue receptive material. For example, according to embodiments of the instant disclosure, open porous metal 100 may have a porosity as low as 55%, 65%, or 75% or as high as 80%, 85%, or 90%. An example of open porous metal 100 is produced using Trabecular Metal™ Technology generally available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 and in Levine, B. R., et al., "Experimental and Clinical Performance of Porous Tantalum in Orthopedic Surgery", Biomaterials 27 (2006) 4671-4681, the disclosures of which are expressly incorporated herein by reference. In addition to tantalum, other metals such as niobium or alloys of tantalum and niobium with one another or with other metals may also be used. Further, other biocompatible metals, such as titanium, a titanium alloy, cobalt chromium, cobalt chromium molybdenum, tantalum, or a tantalum alloy may also be used.

Additionally, embodiments of open porous metal 100 may comprise a Ti-6Al-4V ELI alloy, such as Tivanium® Alloy which is available from Zimmer, Inc., of Warsaw, Ind., Tivanium® is a registered trademark of Zimmer, Inc. Open porous metal 100 may also comprise a fiber metal pad or a sintered metal layer, such as a CSTi™, Cancellous-Structured Titanium™ coating or layer, for example. CSTi™ porous layers are manufactured by Zimmer, Inc., of Warsaw, Ind. CSTi™ is a trademark of Zimmer, Inc.

In other embodiments, open porous metal 100 may comprise an open cell polyurethane foam substrate coated with Ti-6Al-4V alloy using a low temperature arc vapor deposition process. Ti-6Al-4V beads may then be sintered to the surface of the Ti-6Al-4V-coated polyurethane foam substrate. Additionally, another embodiment of open porous metal 100 may comprise a metal substrate combined with a Ti-6Al-4V powder and a ceramic material, which is sintered under heat and pressure. The ceramic particles may thereafter be removed leaving voids, or pores, in the substrate. Open porous metal 100 may also comprise a Ti-6Al-4V powder which has been suspended in a liquid and infiltrated and coated on the surface of a polyurethane substrate. The Ti-6Al-4V coating may then be sintered to form a porous metal structure mimicking the polyurethane foam substrate. Further, another embodiment of open porous metal 100 may comprise a porous metal substrate having particles, comprising altered geometries, which are sintered to a plurality of outer layers of the metal substrate.

Additionally, open porous metal component 100 may be fabricated according to electron beam melting (EBM) and/or laser engineered net shaping (LENS). For example, with EBM, metallic layers (comprising one or more of the biomaterials, alloys, and substrates disclosed herein) may be coated (layer by layer) on an open cell substrate using an electron beam in a vacuum. Similarly, with LENS, metallic powder (such as a titanium powder, for example) may be deposited and coated on an open cell substrate by creating a molten pool (from a metallic powder) using a focused, high-powered laser beam.

Open porous metal 100 may also be fabricated such that it comprises a variety of densities in order to selectively tailor the structure for particular applications. In particular, as discussed in the above-incorporated U.S. Pat. No. 5,282,861, open porous metal 100 may be fabricated to virtually any desired density, porosity, and pore size (e.g., pore diameter), and can thus be matched with the surrounding natural tissue in order to provide an improved matrix for tissue ingrowth and mineralization.

Additionally, according to the instant disclosure, open porous metal 100 may be fabricated to comprise substantially uniform porosity, density, and/or void (pore) size throughout, or to comprise at least one of pore size, porosity, and/or density being varied. For example, open porous metal 100 may have a different pore size and/or porosity at different regions, layers, and surfaces of open porous metal 100. The ability to selectively tailor the structural properties of open porous metal 100 enables tailoring of open porous metal 100 for distributing stress loads throughout the surrounding tissue and promoting specific tissue ingrown within open porous metal 100.

Referring to FIGS. 2a and 2b, two embodiments of open porous metal 100 comprising different pore sizes and porosity at different regions or surfaces, are shown. With reference to FIG. 2a, open porous metal 100a comprises first layer 101a, second layer 103a, first exposed surface region 106a, interface region 107a, and second exposed porous surface region 108a. As illustrated, the nominal pore size of open porous metal 100a is relatively greater in first layer 101a and at first exposed porous surface region 106a as compared to second layer 103a and second exposed porous surface region 108a. In some embodiments of open porous metal 100a, the alteration in pore size and porosity may gradually occur between first layer 101a and second layer 103a to form a gradually increasing or decreasing pore size gradient. In other embodiments of open porous metal 100a, the change in pore size and porosity may be defined and localized at interface region 107a, such as illustrated in FIG. 2a.

Referring to FIG. 2b, another illustrative embodiment of open porous metal 100 is provided. As shown in FIG. 2b, open porous metal 100b, according to the instant disclosure, may comprise first layer 101b, second layer 103b, first exposed porous surface region 106b, interface region 107b, and second exposed porous surface region 108b, Interface region 107b of open porous metal 100b comprises interface substrate 110 positioned between first layer 101b having greater pore size and decreased porosity, and second layer 103b having smaller pore size and greater porosity. According to the embodiment of open porous metal 100 depicted in FIG. 2b, first layer 101b may be affixed to first surface 112 of interface substrate 110 and second layer 103b is affixed to second surface 114 of interface substrate 110. First layer 101b and second layer 103b may be diffusion bonded to first surface 112 and second surface 114 of interface substrate 110, respectively, using applied pressure at an elevated temperature for an appreciable period of time.

Embodiments of open porous metal 100, such as illustrated in FIGS. 2a and 2b, may comprise a reticulated vitreous carbon (RVC) substrate of a uniform pore size having a biocompatible metal, such as tantalum, infiltrated and coated thereon such as described in the above-incorporated U.S. Pat.

No. 5,282,861. According to the instant disclosure, in order to form a porous metal having varying pore sizes, a greater amount of the biocompatible metal may be infiltrated and coated on the carbon substrate in the second layer than in the first layer, resulting in the second layer having decreased pore size. This may be accomplished by masking a portion of the carbon substrate during the infiltration and deposition process, or, following an initial extent of infiltration and deposition of the metal, by at least partially filling a sacrificial material into the pores of one of the layers, followed by carrying out further infiltration and deposition of the metal into the pores of the other layer and then removing the sacrificial material.

With regard to open porous metal 100b, illustrated in FIG. 2b, first layer 101b and second layer 103b may also be affixed to first surface 112 and second surface 114 of interface substrate 110, respectively, by an infiltration and deposition welding process in which the substrates, perhaps following an initial extent of infiltration and deposition of the metal into the substrates as separate components, are held against one another followed by exposing the combined substrate to a further extent of infiltration and deposition of the metal to concurrently coat and thereby fuse the substrates together. In a further embodiment, the substrates may be fused together by a resistance welding process using localized heat generated through electric resistance.

According to exemplary embodiments of the orthopaedic implants disclosed herein, first exposed porous surface region 106 of open porous metal 100 may comprise a bone contacting surface and second exposed porous surface region 108 of open porous metal 100 may comprise a soft tissue contacting surface. According to these embodiments, the voids or pores (defining channels 104) at first exposed porous surface region 106 may comprise pore diameters of as low as approximately 40, 60 or 100 µm to as high as approximately 250, 300, or 350 µm, any value there between, or any value within any range delimited by any pair of the foregoing values, for example. Additionally, the pores at second exposed porous surface region 108 may comprise diameters, of as low as approximately 5, 10, or 15 µm to as high as approximately 100, 200, or 300 µm, any value there between, or any value within any range delimited by any pair of the foregoing values, for example.

Additionally, it should also be understood from the instant disclosure that the voids (pores) within one of, or both of, first layer 101 and second layer 103 of open porous metal 100 may comprise varied diameters at different depths within first layer 101 and second layer 103. By way of example, the plurality of pores at second exposed porous surface region 108 may comprise diameters of approximately 200-300 µm. However, the pore diameters may gradually decrease within second layer 103 such that at as little as 2, 3, or 4, to as high as 13, 14, or 15 pore depths, or any value there between, within second layer 103, for example, the plurality of pores may comprise diameters of approximately 5 to 15 µm. Likewise, it should also be understood from the instant disclosure that the pore diameter may gradually increase within first layer 101 or second layer 103. Selective tailoring of pore diameters, disposed at different depths within first layer 101 and second layer 103, according to the instant disclosure, provides an osteoinductive structure and promotes osteogenic and osteoinductive activity, as well as providing a fibroconductive structure and promoting fibrogenic and fibroinductive activity, within the orthopaedic implants and thereby facilitates the regeneration of the soft tissue to bone interface.

Bone and Soft Tissue Growth Factors and Agents.

In addition to comprising selectively tailored pore diameters at different regions throughout open porous metal 100, open porous metal 100 of the orthopaedic implants disclosed herein may also be combined with various bone and soft tissue growth factors or agents. For example, one or more of osteogenic, osteoinductive, angiogenic, angioinductive, fibrogenic, and/or fibroinductive factors or agents may be applied, or coated, on a portion of the exposed porous surfaces of the orthopaedic implants. Further, one or more bone and soft tissue growth factors or agents may be disposed within channels 104 proximal the exposed porous surfaces of open porous metal 100.

Exemplary bone and soft tissue growth factors or agents which may be combined with the orthopaedic implants disclosed herein include, growth factors influencing the attraction, activation, proliferation, differentiation, and organization of all bone cell types such as osteocytes, osteoclasts, osteoblasts, odontoblasts, cementoblasts, and precursors thereof (e.g., stem cells). Additionally, the bone and soft tissue growth factors or agents disclosed herein include growth factors influencing the attraction, proliferation, differentiation, and organization of soft tissue cell types such as fibrocytes, fibroblasts, chondrocytes, tenocytes, ligament cells, and precursors thereof (e.g., stem cells). Further, the bone growth factors disclosed herein also include angiogenic factors, such as vascular endothelial growth factor (VEGF) and angiopoietins for example.

According to the instant disclosure, exemplary bone growth factors or agents include, but are not limited to, bone morphogenic proteins (BMP) such as BMP-1, BMP-2, BMP-3, BMP-4, BMP-5, BMP-6, BMP-7, Transforming growth factor (TGF)-β, platelet derived growth factors, and epidermal growth factor, for example. Additionally, other bone and soft tissue growth factors or agents which may be combined with the orthopaedic implants disclosed herein include bone proteins, such as osteocalcin, osteonectin, bone sialoprotein, lysyloxidase, cathepsin L, biglycan, fibronextin fibroblast growth factor (FGF), platelet derived growth factor, calcium carbonate, and thrombospondin (TSP). Exemplary soft tissue growth factors or agents which may be combined with the orthopaedic implants disclosed herein include fibroblast growth factors (FGF) such as FGF-I, FGF-II, FGF-9, insulin growth factor (IGF)-I, IGF-II, platelet derived growth factor, epithelial growth factors (EGF), and TGF-α, for example.

In addition to the bone and soft tissue growth factors described above, the orthopaedic implants disclosed herein may also be combined with other general cellular growth factors such as angiogenic growth factors, such as VEGF and angiopoietins, in order to promote and support vascularization at and within the soft tissue to bone interface at the orthopaedic implant. Even further, the orthopaedic implants may be combined with various cell types, for example bone cells such as osteoblasts, osteoclasts, cementoblasts, and odontoblasts for example and/or various soft tissue cells, such as tenocytes, chondrocytes, fibrocytes, fibroblasts, and ligament cells. In addition to the various cell types, and various bone and soft tissue growth factors and agents listed above, the orthopaedic implants may also be combined with stem cells in order to further support regeneration of the soft tissue to bone interface at the orthopaedic implants.

According to exemplary configurations of the orthopaedic implants disclosed herein, first exposed porous surface region 106 (FIG. 2a) and second exposed porous surface region 108 (FIG. 2b) may include (e.g., be coated with) one, or a mixture of bone and soft tissue growth factors or agents. Additionally, one, or a mixture of, bone and soft tissue growth factors and agents may be disposed on or within channels 104 of first layer 101 (proximal first exposed porous surface region 106) and second layer 103 (proximal second exposed porous surface region 108). Further, the specific bone and soft tissue growth factors and agents coated on, and possibly disposed on or within portions of the orthopaedic implants, may be selectively tailored for promotion one of either soft tissue or bone growth (at a desired region of the orthopeadic implant).

According to some configurations of the orthopaedic implants disclosed herein, first exposed porous surface region 106 and second exposed porous surface region 108 may include (e.g., be coated with) different bone and soft tissue growth factors and agents. Likewise, channels 104 of first layer 101 (proximal first exposed porous surface region 106) and channels 104 of second layer 103 (proximal second exposed porous surface region 108) may have differing bone and soft tissue growth factors and agents disposed therein. For example, an orthopaedic implant according to the instant disclosure may include one, or a mixture of, osteoinductive and osteogenic growth factors coated on first exposed porous surface region 106 and disposed within channels 104 of first layer 101 (proximal first exposed porous surface region 106). Additionally, the orthopaedic implant may include one, or a mixture of fibrogenic and fibroinductive growth factors coated on second exposed porous surface region 108 and disposed within channels 104 of second layer 103 (proximal second exposed porous surface region 108). Selective tailoring of pore diameters throughout open porous metal 100, in addition to selective coating of the exposed porous surfaces of the orthopaedic implants with bone and soft tissue growth factors as disclosed herein, promotes regeneration of the soft tissue to bone interface at the orthopaedic implants.

Figure 3A:
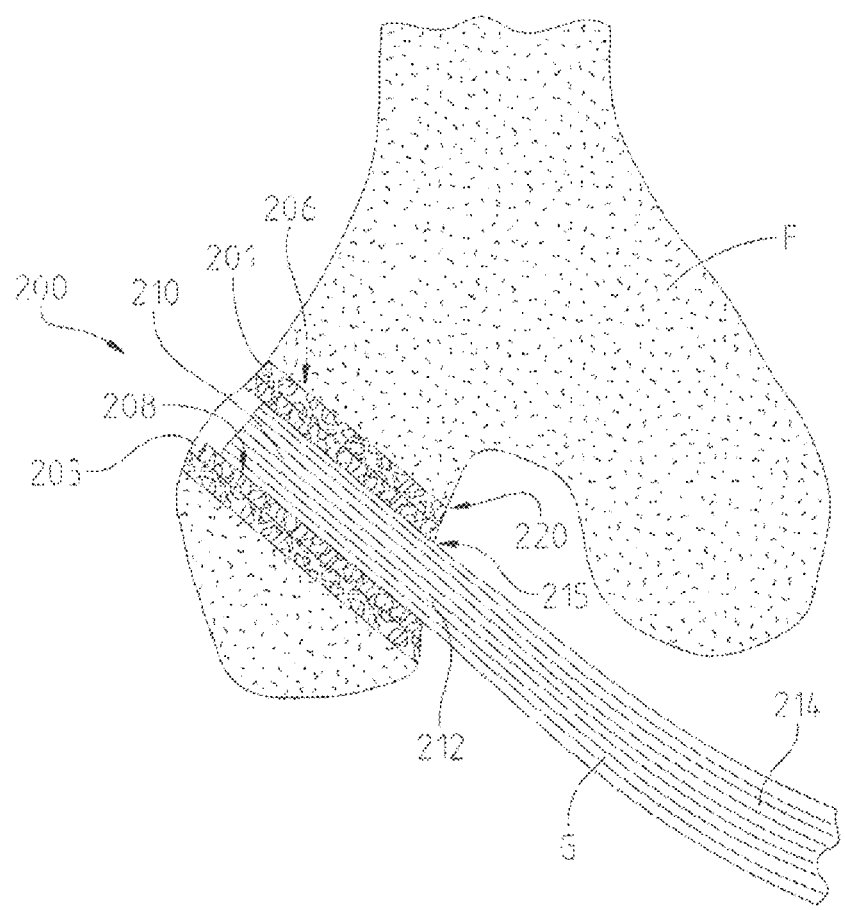
FIG. 3a is a cross-sectional view illustrating an ACL graft secured to a condyle of a femur with an orthopaedic implant according to the present disclosure.

Treatment of an Anterior Cruciate Ligament Injury with an Exemplary Orthopaedic Implant Referring to FIG. 3a, an illustrative embodiment of orthopaedic implant 200 comprising open porous metal 100 (FIG. 1) is depicted. As shown, orthopaedic implant 200 comprises an implant for securing an anterior cruciate ligament ("ACL") or ACL graft G to a bone F. Although FIG. 3a depicts orthopaedic implant 200 securing ACL graft G to a femur (bone F), it should be understood that orthopaedic implant 200 may also be utilized for securing ACL graft G to a tibia.

According to some configurations of the instant disclosure, orthopaedic implant 200 may include first layer 201 (comprising first exposed porous surface region 206 for contacting bone F) and second layer 203 (comprising second exposed porous surface region 208 for contacting ACL graft G). Although orthopaedic implant 200 is depicted in FIG. 3a as comprising two layers (first layer 201 and second layer 203), configurations of orthopaedic implant 200 may also comprise a single layer structure.

As depicted in FIG. 3a, orthopaedic implant 200 also encircles graft securing tunnel 210 such that second exposed porous surface region 208 outlines (e.g., provides a rim around) graft securing tunnel 210. Additionally, while FIG. 3a depicts orthopaedic implant 200 as being substantially tubular with a circular cross-section, configurations of orthopaedic implant 200 may include other forms such as square, rectangular, and oval. In this regard, tubular or tube-like structures with cross sections of any suitable two-dimensional rectilinear or curvilinear shape may be utilized. Further, configurations of orthopaedic implant 200, according to the instant disclosure, may be flexible such that graft securing tunnel 210 can be compressed, thereby allowing second exposed porous surface 208 to contact ACL graft G along substantially all surfaces of ACL graft G when positioned within graft securing tunnel 210.

Configurations of orthopaedic implant 200 may also comprise open porous metal 100 (FIG. 1) having different pore sizes and porosity at different regions or surfaces of orthopaedic implant 200, such as shown in FIGS. 2a and 2b for example. According to some configurations of orthopaedic implant 200, the plurality of pores (voids) within first layer 201 proximal first exposed porous surface region 206 may comprise nominal pore diameters which are greater than the plurality of pores (voids) within second layer 203 proximal second exposed porous surface region 208. According to an exemplary configuration of orthopaedic implant 200, the plurality of pores within first layer 201 proximal first exposed porous surface region 206 may comprise pore diameters of as low as approximately 40, 60, or 100 μm to as high as approximately 250, 300, or 350 μm, any value there between, or any value within any range delimited by any pair of the foregoing values, for example, whereas the plurality of pores within second layer 203 proximal second exposed porous surface region 208 may comprise pore diameters as low as approximately 5, 10, or 15 μm to as high as approximately 200, 250, or 300 μm, any value there between, or any value within any range delimited by any pair of the foregoing values.

In addition to comprising open porous metal 100 (FIG. 1) with different pore sizes and porosities at different regions or surfaces, configurations of orthopaedic implant 200 may also comprise different pore sizes and porosity at different depths throughout open porous metal 100. For example, orthopaedic implant 200 may comprise open porous metal 100 having pores at first exposed porous surface region 206 with pore diameters of approximately 300 μm to 400 μm, for example, whereas the pores disposed 3 to 6 pore diameters within first layer 201 comprise pore diameters of approximately 100 μm to 300 μm. Similarly, orthopaedic implant 200 may comprise open porous metal 100 (FIG. 1) having pores at second exposed porous surface region 208 comprise pore diameters of approximately 200 μm to 300 μm, for example, whereas the pores disposed 3 to 6 pore diameters within second layer 203 comprise pore diameters of approximately 15 μm to 50 μm. As explained herein, variation of pore diameters throughout first layer 201 and second layer 203 allows orthopaedic implant 200 to provide an optimal matrix for providing an osteoinductive and fibroconductive structure and promoting osteogenic and fibrogenic activity, as well as osteoinductive and fibroinductive activity, at select positions within, and along, orthopaedic implant 200.

Additionally, orthopaedic implant 200 may be combined with various bone and soft tissue growth factors or agents as discussed above. For example, a configuration of orthopaedic implant 200 may include a mixture of one or more bone and growth factors coated on at least one of first and second exposed porous surface regions 206, 208. Additionally, a mixture of one or more bone and soft tissue growth factors may be disposed within channels 104 of first and second layers 201, 203 proximal first and second exposed porous surface regions 206, 208.

According to another configuration of orthopaedic implant 200, first exposed porous surface region 206 may be coated with one or more bone growth factors or agents, while second exposed porous surface region 208 may be coated with one or more soft tissue growth factors or agents. Additionally, channels 104 (FIG. 1) of first layer 201 proximal first exposed porous surface region 206 may include one or more bone growth factors or agents disposed therein, while channels 104 of second layer 203 proximal second exposed porous surface region 208 may include one or more soft tissue growth factors or agents disposed therein. As detailed herein, combining orthopaedic implant 200 with select mixtures of bone and soft tissue growth factors and agents (at various positions along and within orthopaedic implant 200), enhances the regeneration of soft tissue to bone interface.

In use, during surgical repair of an ACL injury, orthopaedic implant 200 is placed within bone tunnel 220. Bone tunnel 220 is created during surgery, though reaming, drilling, or any method known in the art, for placement of orthopaedic implant therein. Although bone tunnel 220 is shown in FIG. 3a as extending substantially through a condyle of femur F, it should be understood that bone tunnel may extend only partially within femur F as well.

As depicted in FIG. 3a, first end 212 of ACL graft G is inserted through first opening 215, defined by orthopaedic implant 200, and positioned within graft securing tunnel 210. According to configurations of orthopeadic implant 200, first end 212 of ACL graft G may be secured within graft securing tunnel 210 by compressing orthopaedic implant 200 such that substantially all of first end 212 of ACL graft G is contacted by second open exposed porous surface region 208 of orthopaedic implant 200, According to other configurations of orthopaedic implant 200, first end 212 of ACL graft G may be initially secured within graft securing tunnel 210 by way of a securing anchor, such as an anchor screw or another type of anchoring device, for example. According to such configurations, first end 212 of ACL graft is affixed to the anchor and the anchor is then the secured within graft securing tunnel 210. Further, in some configurations, securing anchors may be comprised in part or entirely of open porous metal 100 (FIG. 1) as described herein.

Upon securing first end 212 of ACL graft G within graft securing tunnel 210, orthopaedic implant 200 is positioned within bone tunnel 220. As shown in FIG. 3a, orthopaedic implant 200 is positioned within bone tunnel 220 such that first exposed porous surface region 206 contacts bone F (which has been reamed or drilled) and second open porous surface 208 continues contacting first end 212 of ACL graft G positioned within graft securing tunnel 210. As depicted in FIG. 3a, second end 214 of ACL graft G extends out of graft securing tunnel 210 through first opening 215.

Orthopeadic implant 200 may be secured within bone tunnel 220 by way of the high coefficient of friction of first exposed porous surface 206, imparted by struts 150 (FIG. 1) of open porous metal 100 comprising first exposed porous surface region 206, as described in detail in Bobyn J. D., et al, "Characterization of new porous tantalum biomaterial for reconstructive orthopaedics", Scientific Exhibition: 66$^{th}$ Annual Meeting of the American Academy of Orthopaedic Surgeons; 1999; Anaheim Calif., the disclosure of which is expressly incorporated herein by reference. First exposed porous surface region 206 may have a coefficient of friction (in contact with cancellous bone) which is sixty-five percent greater than the coefficient of friction of cortical bone (in contact with cancellous bone), for example, as described in detail in Zhang Y. et al., "Interfacial factional behavior: Cancellous bone, cortical bone, and a novel porous tantalum biomaterial", Journal of Musculoskeletal Research, 1999; 3(4): 245-251, the disclosure of which is expressly incorporated herein by reference.

According to configurations of orthopaedic implant 200 in which the high coefficient of friction of first exposed porous surface region 206 secures orthopaedic implant 200 within bone tunnel 220, the coefficient of friction of first exposed porous surface region 206 provides an initial fixation of orthopaedic implant 200 to the bone F defining bone tunnel 210. The initial fixation secures orthopaedic implant 200 within bone tunnel 220 for a period of time following implantation. Additionally, as explained above, open porous metal 100 further provides a matrix for bone ingrowth and mineralization. Bone ingrowth, within open porous metal 100 comprising first exposed porous surface region 206 and first layer 201, thereby provides a rigid and secure secondary fixation of orthopaedic implant 200 within bone tunnel 220.

Additionally, although not depicted, configurations of orthopaedic implant 200 may be secured within bone tunnel 220 with an affixation screw or with an adhesive. First end 212 of ACL graft G may also be secured within graft securing tunnel 210 by way of an affixation screw or an adhesive.

According to some configurations of orthopaedic implant 200, ACL graft G may be secured within graft securing tunnel 210 by way of the high coefficient of friction of second exposed porous surface region 208, imparted by struts 150 (FIG. 1) of open porous metal 100 comprising second exposed porous surface region 208. Further, the coefficient of friction of second exposed porous surface 208 may differ from the coefficient of friction of first exposed porous surface region 206, or may be approximately the same as the coefficient of friction of first exposed porous surface region 206.

According to configurations of orthopeadic implant 200 in which the coefficient of friction of second exposed porous surface region 208 secures ACL graft G within graft securing tunnel 210, the coefficient of friction of second exposed porous surface region 208 provides an initial fixation of ACL graft G to the second exposed porous surface region 208. The initial fixation secures ACL graft G within graft securing tunnel 210 for a period of time following implantation. However, as explained above, open porous metal 100 further provides a matrix for soft tissue ingrowth and mineralization. Soft tissue ingrowth, within open porous metal 100 comprising second exposed porous surface region 208 and second layer 203, thereby provides a rigid and secure secondary fixation of ACL graft G within graft securing funnel 210.

Figure 3B:
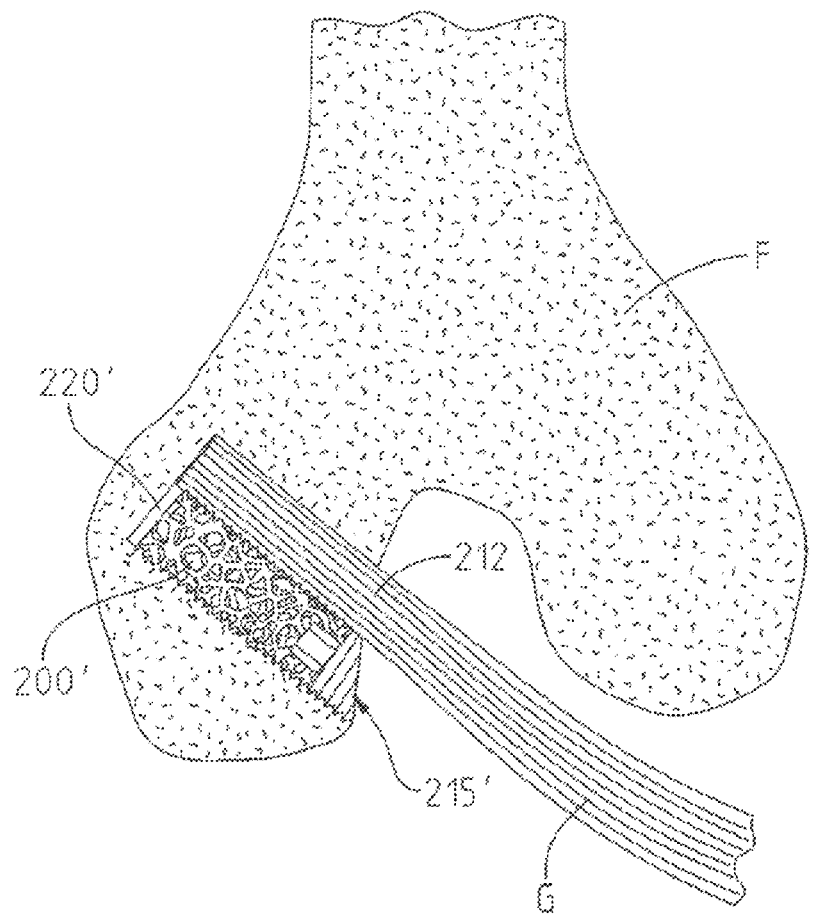
FIG. 3b is a cross-sectional view illustrating an ACL graft secured to a condyle of a femur with another embodiment of an orthopaedic implant according to the present disclosure.

Referring to FIG. 3b, an illustrative configuration of orthopaedic implant 200' is depicted. As shown, orthopaedic implant 200' comprises screw 250 or dowel (not shown) for securing an ACL graft G within bone tunnel 220' of bone F. According to configurations of orthopaedic implant 200', screw 250 (or dowel) comprises open porous metal 100 (FIG. 1) as described herein, advantageously promoting bone and/or soft tissue ingrowth along all sides of, and throughout, screw 250. Additionally, orthopaedic implant 200' may also be combined with one or more bone and/or soft tissue growth factors or agents as discussed above. Further, although FIG. 3b depicts orthopaedic implant 200' securing ACL graft G to a femur (bone F), it should be understood that orthopaedic implant 200' may also be utilized for securing ACL graft G to a tibia.

While configurations of orthopaedic implant 200 and 200', disclosed herein, have been described and depicted in use for repairing an ACL, configurations of orthopaedic implant 200 and 200' may also be used in the repair of other soft tissue injuries. For example, orthopaedic implant 200 and 200' may also be useful in repair of other knee ligaments, elbow ligaments and tendons, shoulder ligaments and tendons, biceps tendon and ligaments, and ankle ligaments and tendons.

Treatment of a Rotator Cuff injury with an Exemplary Orthopaedic Implant.

Figure 4:
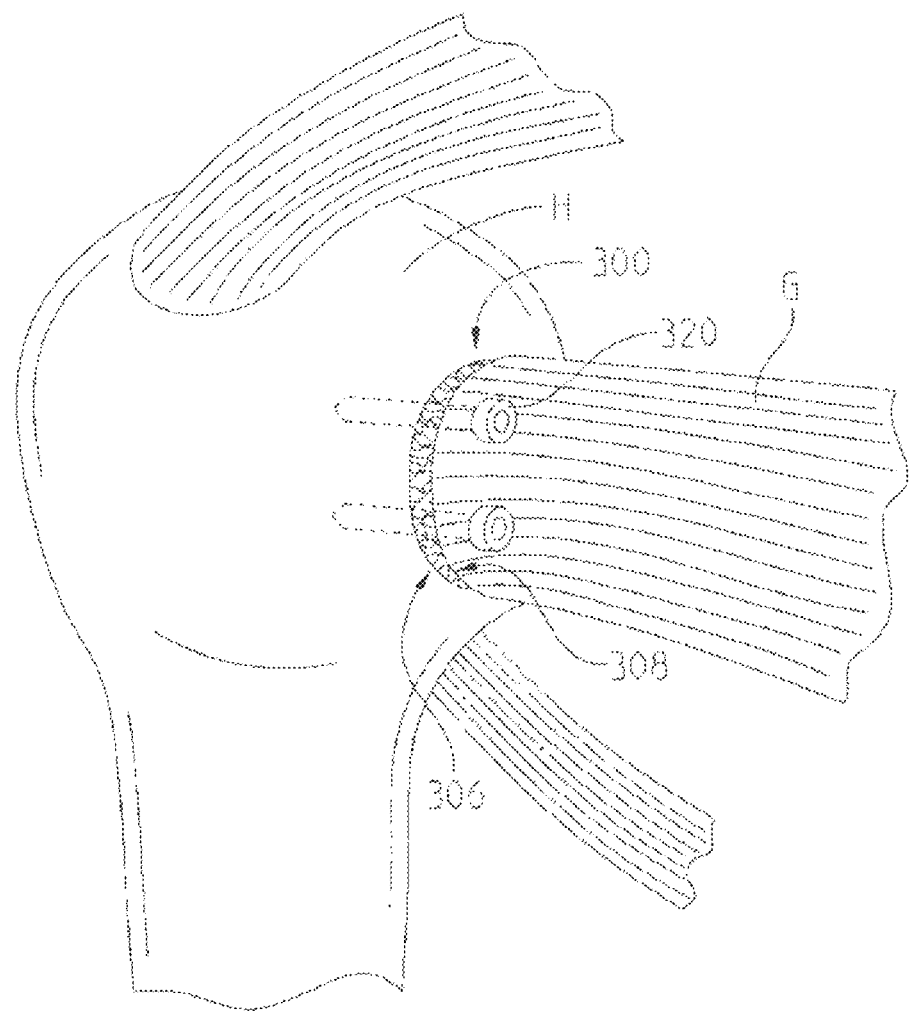
FIG. 4 is a perspective view illustrating a rotator cuff tendon secured to a humerus with an orthopaedic implant according to the present disclosure.

Referring to FIG. 4, another illustrative embodiment of orthopaedic implant 300 comprising open porous metal 100 is depicted. As shown, orthopaedic implant 300 comprises an implant for securing a rotator cuff (e.g., a subscapularis tendon or soft tissue graft G), or a portion thereof, to bone H (illustrated as a humerus).

According to some configurations of the instant disclosure, orthopaedic implant 300 may include first exposed porous surface region 306 (for contacting bone H) and second exposed porous surface region 308 (for contacting soft tissue G). Orthopaedic implant 300, as depicted in FIG. 4, may also include one or more anchoring screws 320 for securing orthopaedic implant 300 to bone H, and/or for securing graft G to orthopaedic implant 300. In some configurations of orthopaedic implant 300, anchoring screws 320 may partially, or entirely, comprise open porous metal 100 (FIG. 1) as described herein.

As shown in FIG. 4, orthopaedic implant 300 comprises a thin sheet of open porous metal 100 (FIG. 1). According to some configurations, orthopaedic implant 300 may also be malleable such that, during a surgical procedure, orthopaedic implant 300 may advantageously be shaped and sized to a desired form. However, while orthopaedic implant 300 is depicted and described herein as a thin sheet of open porous metal 100, configurations of orthopaedic implant 300 may also comprise open porous metal 100 having a first layer and a second layer (similar to orthopaedic implant 200 depicted in FIG. 3a). Additionally, while orthopaedic implant 300 is depicted in FIG. 4 as being circular or disc-like, configurations of orthopaedic implant 300 may comprise any number of forms such as a square, rectangle, oval, or other polygonal shape, for example.

Similar to embodiments of orthopaedic implant 200 (FIG. 3a), orthopaedic implant 300 may comprise open porous metal 100 (FIG. 1) having different pore sizes and porosity at different regions or surfaces of orthopeadic implant 300. For example, configurations of orthopaedic implant 300 may include the plurality of pores (voids) at first exposed porous surface region 306 having nominal pore diameters which are greater than the plurality of pores (voids) at second exposed porous surface region 308. Further, configurations of orthopaedic implant 300 may also comprise different pore sizes and porosity at different depths throughout open porous metal 100.

Additionally, as described herein, orthopaedic implant 300 may be combined with various bone and soft tissue growth factors or agents. For example, a configuration of orthopaedic implant 300 may include a mixture of one or more bone and soft tissue growth factors coated on at least one of first and second exposed porous surface regions 306, 308. A mixture of one or more bone and soft tissue growth factors may also be disposed on or within channels 104 (FIG. 1) of open porous metal 100 (comprising orthopaedic implant 300) proximal first and second exposed porous surface regions 306, 308. Further, configurations of orthopaedic implant 300 may include first exposed porous surface region 306 being coated with one or more bone growth factors or agents, while second exposed porous surface region 308 is coated with one or more soft tissue growth factor or agent.

In use, during surgical repair of a rotator cuff injury, orthopaedic implant 300 may be secured to humerus H with anchoring screws 320. Prior to securing orthopaedic implant 300 to humerus H, a portion of humerus H may be prepared for securing orthopaedic implant 300 thereto, for example, by reaming or grinding a portion of humerus H. As shown in FIG. 4, orthopaedic implant 300 is secured to humerus H such that first exposed porous surface region 306 contacts humerus H and second exposed porous surface region 308 contacts soft tissue G. Additionally, soft tissue G may also be secured to second exposed porous surface region 308 of orthopaedic implant 300 with anchoring screws 320. In some configurations of orthopaedic implant 300, soft tissue G may be secured to second exposed porous surface region 306 by way of the coefficient of friction of second exposed porous surface region 308, imparted by struts 150 (FIG. 1) of open porous metal 100 comprising second exposed porous surface region 308.

According to configurations of orthopeadic implant 300 in which orthopeadic implant 300 is secured to bone h (and/or soft tissue G) by way of the high coefficient of friction of open porous metal 100, the coefficient of friction provides an initial fixation for securing orthopaedic implant 300 to bone H (and/or soft tissue G). As explained herein, the initial fixation secures orthopaedic implant 300 to bone H, and soft tissue G to (second exposed porous surface region 308 of) orthopaedic implant 300, for a period of time following implantation. However, ingrowth and mineralization of bone H within first exposed porous surface region 306 (and first layer 301), and soft tissue G within second exposed porous surface region 308 (and second layer 303), thereby provides a rigid and secure secondary fixation of soft tissue G to orthopaedic implant 300 and orthopaedic implant 300 to bone H.

While configurations of orthopaedic implant 300, disclosed herein, have been described and depicted for use in repairing a rotator cuff injury, configurations of orthopaedic implant 300 may also be useful in the repair of other soft tissue injuries. For example, orthopaedic implant 300 may also be useful in repair of knee ligaments, elbow ligaments and tendons, and ankle ligaments and tendons.

Treatment of Achilles Tendon Injury with an Exemplary Orthopaedic Implant.

Further, orthopaedic implant 300 may also be useful in the repair of Achilles tendon injuries such as ruptures. Referring to FIGS. 5a and 5b, illustrative embodiments of orthopaedic implant 300' and 300", respectively, are shown securing an achilles tendon or soft tissue graft G to a bone C in the ankle region, such as a calcaneus bone. Similar to configurations of orthopaedic implant 300 depicted in FIG. 4, above, orthopaedic implants 300' and 300" include first exposed porous surface region 306', 306" (for contacting bone and/or soft tissue) comprised of open porous metal 100 (FIG. 1). Orthopaedic implant 300', shown in FIG. 5a also includes second exposed porous surface region 308' (for contacting soft tissue) comprised of open porous metal 100.

Referring to FIGS. 5a and 5b, orthopaedic implants 300', 300" comprise a thin sheet of open porous metal 100 (FIG. 1). According to some configurations, orthopaedic implants 300', 300" may also be flexible such that, during a surgical procedure, orthopaedic implants 300', 300" may advantageously be shaped and sized to a desired form. Similar to configurations of orthopaedic implant 300, open porous metal 100 comprising orthopaedic implants 300', 300" may also have different pore sizes and porosity at different regions or surfaces, and at different depths throughout orthopaedic implants 300', 300". Further, configurations of orthopaedic implants 300', 300", as with orthopaedic implant 300 (FIG. 4), may also be combined with one or more bone and soft tissue growth factors or agents.

Referring to FIG. 5a, in use during surgical repair of an Achilles tendon injury orthopaedic implant 300' may be secured to a bone C in the ankle region of a leg, for example a calcaneus bone. Advantageously, orthopaedic implant 300' may be shaped and sized (during the surgical procedure) to the size and contour of the bone C. Further, orthopaedic implant 300' may be secured to bone C by way of anchoring screws 320 or an adhesive. As shown, orthopaedic implant 300' is secured to bone C such that first exposed porous surface region 306' contacts bone C and second exposed porous surface region 308' contacts soft tissue G. Soft tissue G is secured to second exposed porous surface region 308' of orthopaedic implant 300', for example, with anchoring screws 320, surgical sutures, or the like. Additionally, in some configurations of orthopaedic implant 300', soft tissue G may be secured to first exposed porous surface region 306' or by way of the coefficient of friction of second exposed porous surface region 308'.

Referring to FIG. 5b, another configuration of orthopaedic implant 300" for use during surgical repair of an Achilles tendon injury is shown. According to FIG. 5b, soft tissue G is secured to bone C, or is held against bone C by orthopaedic implant 300", As shown, a portion of first exposed porous surface region 306" of orthopaedic implant 300" contacts soft tissue G and presses soft tissue G against bone C. Portions of first exposed porous surface region 306' not contacting soft tissue G, are contoured to contact bone C. Orthopaedic implant 300' may be secured to soft tissue G and bone C by way of anchoring screws 320 or an adhesive, such that the soft tissue G is also secured to bone C and first exposed porous surface region 306" of orthopaedic implant 300", Further, similar to configurations of orthopaedic implant 300' shown in FIG. 5a, orthopaedic implant 300' may advantageously be shaped and sized (during the surgical procedure) to a desired size and shape.

According to configurations of orthopeadic implant 300', 300" in which orthopeadic implant 300', 300' is secured to bone C, and/or soft tissue G is secured to orthopaedic implant 300', 300", by way of the high coefficient of friction of open porous metal 100, the coefficient of friction provides an initial fixation for securing orthopaedic implant 300', 300" to bone C, and/or soft tissue G to orthopaedic implant 300', 300". As explained above, the initial fixation secures orthopaedic implant 300', 300" to bone C, and/or soft tissue G to orthopaedic implant 300', 300", for a period of time following implantation. However, ingrowth and mineralization of bone C within first exposed porous surface region 306', 306", and soft tissue G within second exposed porous surface region 308' or first exposed porous surface region 306", thereby provides a rigid and secure secondary fixation of soft tissue G to orthopaedic implant 300', 300" and orthopaedic implant 300', 300" to bone C.

Further, in some configurations of orthopaedic implant 300", open porous metal 100 (FIG. 1) comprising portions (or regions) of first exposed porous surface region 306" may have different pore sizes and porosities. For example, the portion of first exposed porous surface region 306" contacting (and proximal to) soft tissue G may comprise pores (voids) having nominal pore diameters which are smaller than the pores of the portion of first exposed porous surface region 306" which contact bone C.

Further, configurations of orthopaedic implant 300" may also include portions of first exposed porous surface region 306" being combined with different mixtures of bone and soft tissue growth factors and agents. For example, the portion of first exposed porous surface region 306" contacting (and proximal to) soft tissue G may be combined with one or more soft tissue growth factors and agents, whereas the portion of first exposed porous surface region 306" contacting bone C may be combined with one or more bone growth factors or agents.

While configurations of orthopaedic implants 300", 300" disclosed herein, have been described and depicted for use in repairing an Achilles tendon injury, configurations of orthopaedic implants 300', 300" may also be useful in the repair of other soft tissue injuries. For example, orthopaedic implants 300', 300" may also be useful in repair of knee ligaments and tendons, elbow ligaments and tendons, and other ankle ligaments and tendons.

Anchor Screw Embodiment of Orthopaedic implant

Figure 6:
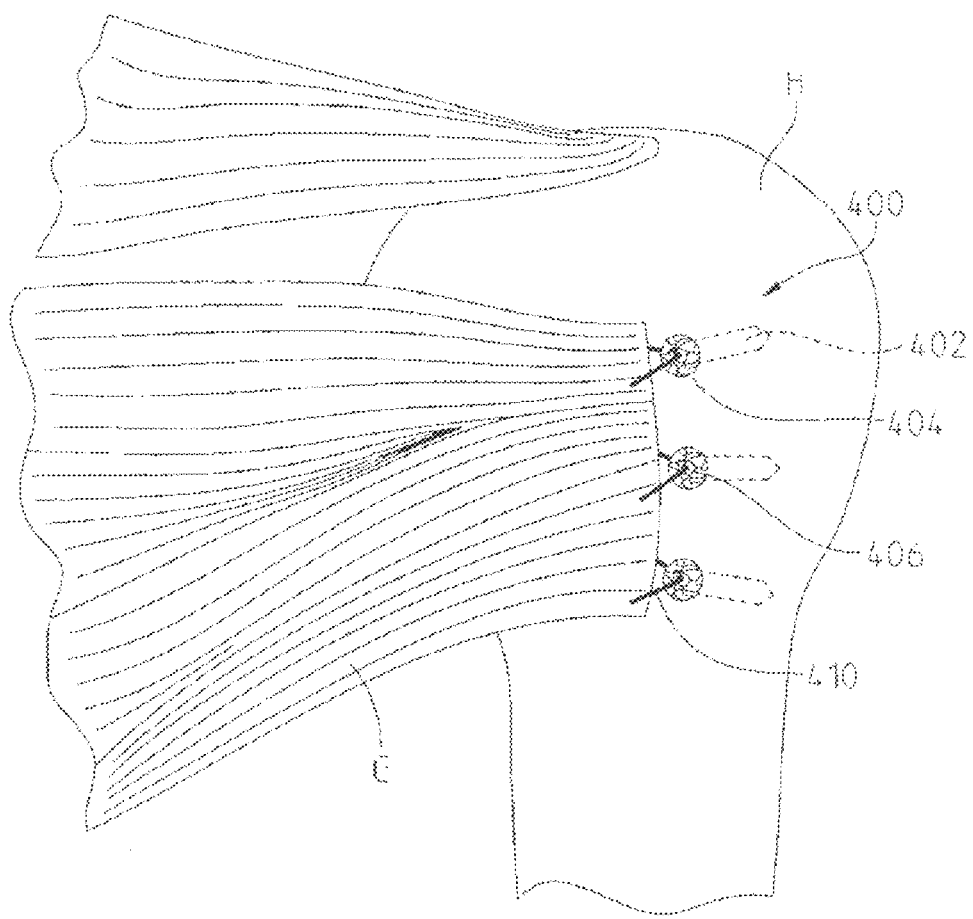
FIG. 6 is a perspective view illustrating a rotator cuff tendon secured to a humerus with another embodiment of an orthopaedic implant according to the present disclosure.

Referring to FIG. 6, an illustrative embodiment of orthopaedic implant 400 comprising a (or a plurality of) threaded anchor screw is shown. Orthopaedic implant 400 may partially or entirely comprise open porous metal 100 (FIG. 1). As shown, orthopaedic implant 400 may be used for securing a rotator cuff (e.g., a subscapulars tendon or soft tissue graft G), or a portion thereof, to bone H (illustrated as a humerus).

As shown in FIG. 6, orthopaedic implant 400 includes thread component 402 (for contacting bone H and securing orthopaedic implant 400 therein) and aperture 404 (for receiving surgical sutures therethrough).

Additionally, according to some configurations of the present disclosure, open porous metal 100 (FIG. 1) comprising orthopaedic implant 400 may have different pore sizes and porosity at different regions or surfaces of orthopeadic implant 400. For example, configurations of orthopaedic implant 400 may include the plurality of pores (voids) of thread component 402 having nominal pore diameters which are greater than the pore diameters of the pores proximal aperture 404. Further, configurations of orthopaedic implant 400 may also include the coefficient of friction of the open porous metal 100 defining aperture 404 being lower than the coefficient of friction of open porous metal 100 comprising thread component 402.

Additionally, orthopaedic implant 400 may be combined with various bone and soft tissue growth factors or agents. For example, a configuration of orthopaedic implant 400 may include a mixture of one or more bone and soft tissue growth factors coated on at least thread component 402. Further, configurations of orthopaedic implant 400 may also include one or more soft tissue growth factor or agents coated on open porous metal 100 defining aperture 404.

In use, during surgical repair of a rotator cuff injury, thread component 402 of orthopaedic implant 400 may be securely screwed or drilled into humerus H. As depicted in FIG. 6, one or more orthopaedic implants 400 may be used. Surgical sutures 410 are threaded into a first end of soft tissue graft G, and threaded through apertures 404 of the one or more orthopaedic implants 400, Soft tissue G is secured to orthopaedic implant 400, and tension applied to soft tissue G, by way of securing surgical sutures 410 to orthopaedic implant 400 at apertures 404.

While configurations of orthopaedic implant 400 have been described and depicted herein as comprising a threaded anchor screw, embodiments of orthopaedic implant 400 may also comprise a dowel component and a dowel sleeve component (not shown). According to such configurations, soft tissue G is secured to a first end of the dowel component. The dowel component may then either be secured in a previously prepared bone tunnel, or may be secured within a dowel sleeve component secured in a bone tunnel. As described herein, configurations of orthopaedic implant 400 comprising a dowel and dowel sleeve component may also comprise open porous metal 100 (FIG. 1) having pores (voids) comprising varying pore diameters. For example, configurations of orthopaedic implant 400 may include open porous metal 100 of dowel component having pore diameters which are smaller than the pore diameters of open porous metal 100 of dowel sleeve component.

Orthopaedic implant 400, while having been disclosed and described herein for use in repairing rotator cuff injuries, may also be useful in the repair of other soft tissue injuries. For example, orthopaedic implant 400 may also be useful in repair of knee ligaments, elbow ligaments and tendons, and ankle ligaments and tendons.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fail within the limits of the appended claims.

EXAMPLES

The following non-limiting Examples illustrate various features and characteristics of the present invention, which is not to be construed as limited thereto.

Example 1

Cellular Responses to Various Porous Tantalum Surfaces

I. Introduction.

The aim of the present example disclosed herein was to evaluate interactions of human bone and soft tissue growth factors with an open porous metal according to the present disclosure. The examples provided herein further aim to evaluate osteoblast and fibroblast cell attachment, ingrowth and proliferation with an open porous metal according to the present disclosure.

II. Methods and Materials.

Figure 7:
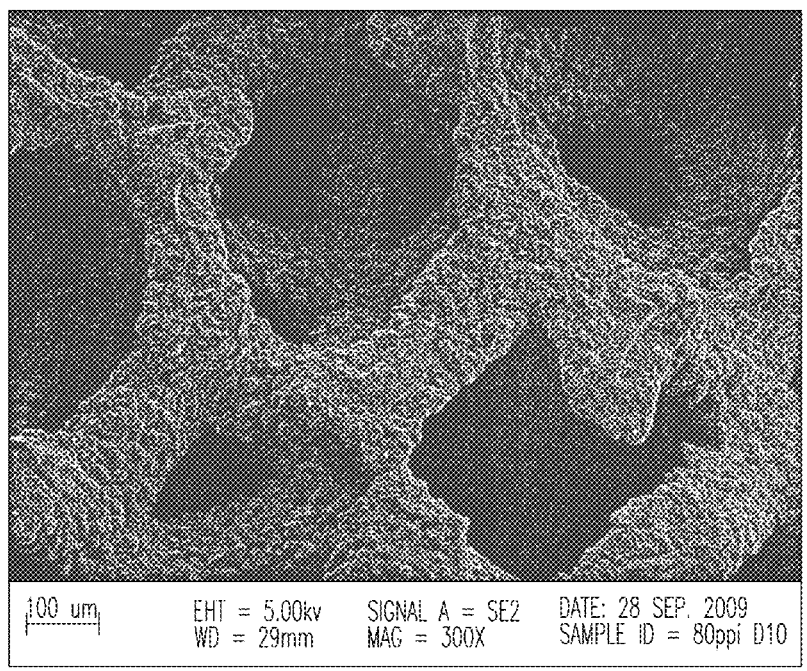
FIG. 7 is a scanning electron microscopy image of a porous tantalum disc utilized in the Examples presented herein.

Circular porous tantalum discs having a diameter of approximately 10 mm and a thickness of 3 mm, were utilized in the Examples presented herein (see FIG. 7). Porous tantalum (Trabecular Metal™, Zimmer, Inc., Warsaw, Ind.) is a form of open porous metal which has been utilized as an implantable material in clinical orthopaedic applications. The porous tantalum discs utilized in the present Examples were fabricated according to a chemical vapor deposition/infiltration technique, as described herein. The discs were also terminally sterilized using gamma irradiation. Control discs comprised gamma sterilized polished non-porous titanium discs having the same dimensions as the porous tantalum discs were also utilized.

Human osteoblasts (ATCC, CRL-1427) and human skin fibroblasts (ATCC, CRL-2522) were seeded onto the porous tantalum and Ti discs at a density of $2\times10^4$ cells per disc, and thereafter cultured in Eagle's Minimum Essential Medium with ten percent fetal bovine serum and one percent antibiotics at thirty-seven degrees Celsius in a humidified incubator. Following ten days of culture, cells on the discs were fixed with gluteraldehyde then dehydrated sequentially using ethanol series (50%, 70%, 80%, 90%, 95%, and 100%) for ten minutes each. The discs were coated with Pt/Pd and then viewed using scanning electron microscopy. Cell proliferation was quantified using the nonradioactive cell proliferation (MTS) assay from Promega (n=3). One-way ANOVA was used for performing statistical analysis ($p<0.05$).

III. Results and Conclusions.

Figure 8:
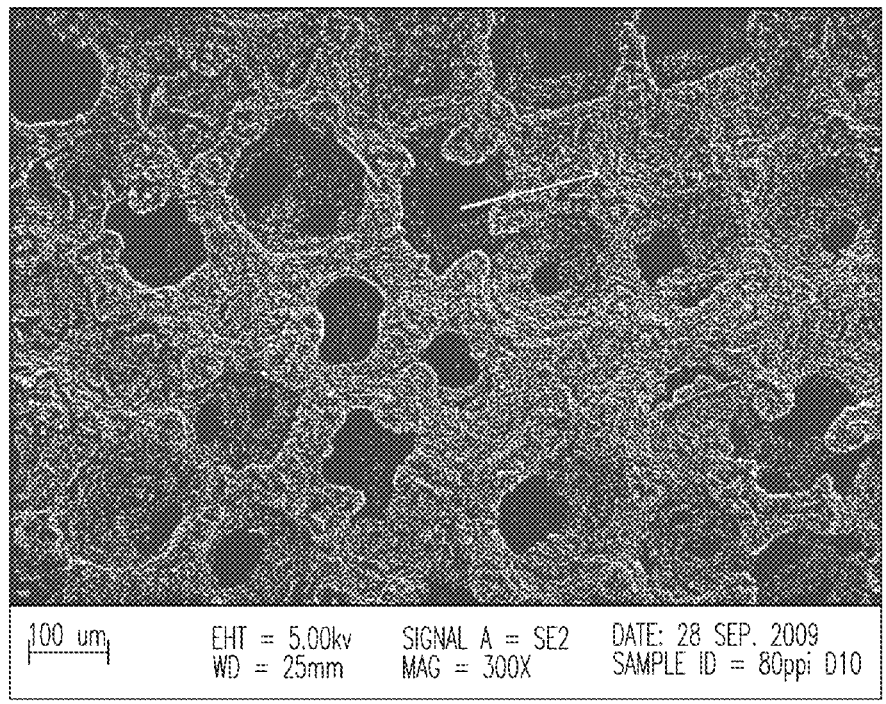
FIG. 8 is a scanning electron microscopy image of human osteoblast growth within a porous tantalum disc utilized in the Examples presented herein, including arrows showing cell proliferation along the periphery of the pores of the porous tantalum discs.

The Examples disclosed herein demonstrated that the porous tantalum discs supported attachment and proliferation of osteoblasts and fibroblasts. Referring to FIG. 8, growth of human osteoblasts upon a porous tantalum disc after ten days culture according to the present Examples, is shown. As shown in FIG. 8, the osteoblasts produced extracellular matrix covering the TM surfaces and migrated into the pores of the discs.

Figure 9:
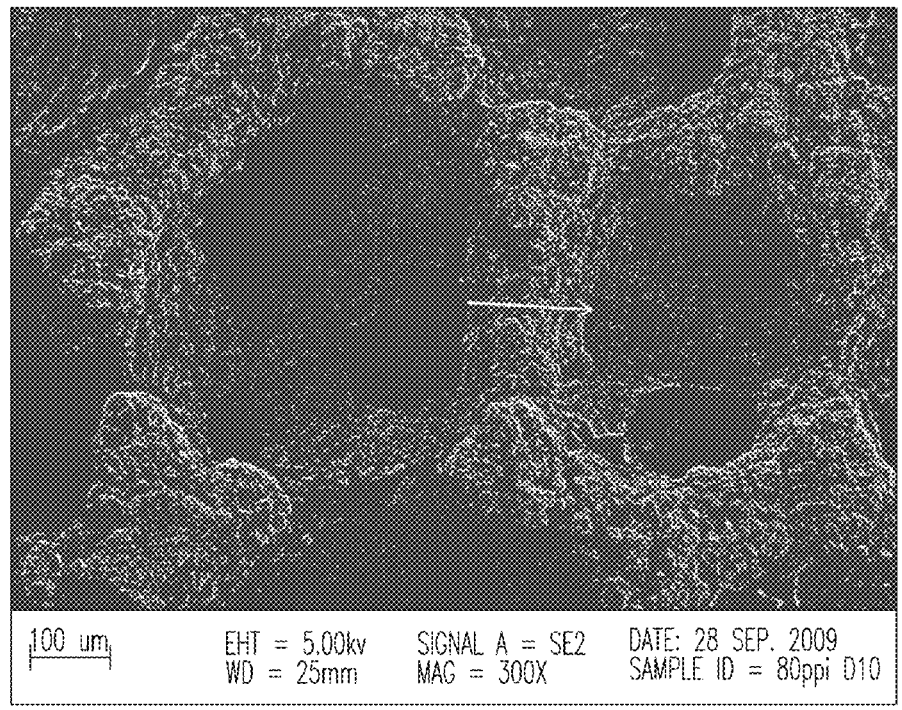
FIG. 9 is a scanning electron microscopy image of human fibroblast growth within a porous tantalum disc utilized in the Examples presented herein, including arrows showing cell proliferation along the periphery of the pores of the porous tantalum disc.

Referring to FIG. 9, growth of human fibroblasts upon the porous tantalum discs after ten days culture according to the present Examples, is shown. As shown in FIG. 9, the majority of fibroblasts proliferated on the porous tantalum skeleton and along the periphery of the pores. The fibroblasts produced less extracellular matrix than osteoblasts did, and a smaller percentage of fibroblasts migrated into the pores after ten days of culture.

Figure 10:
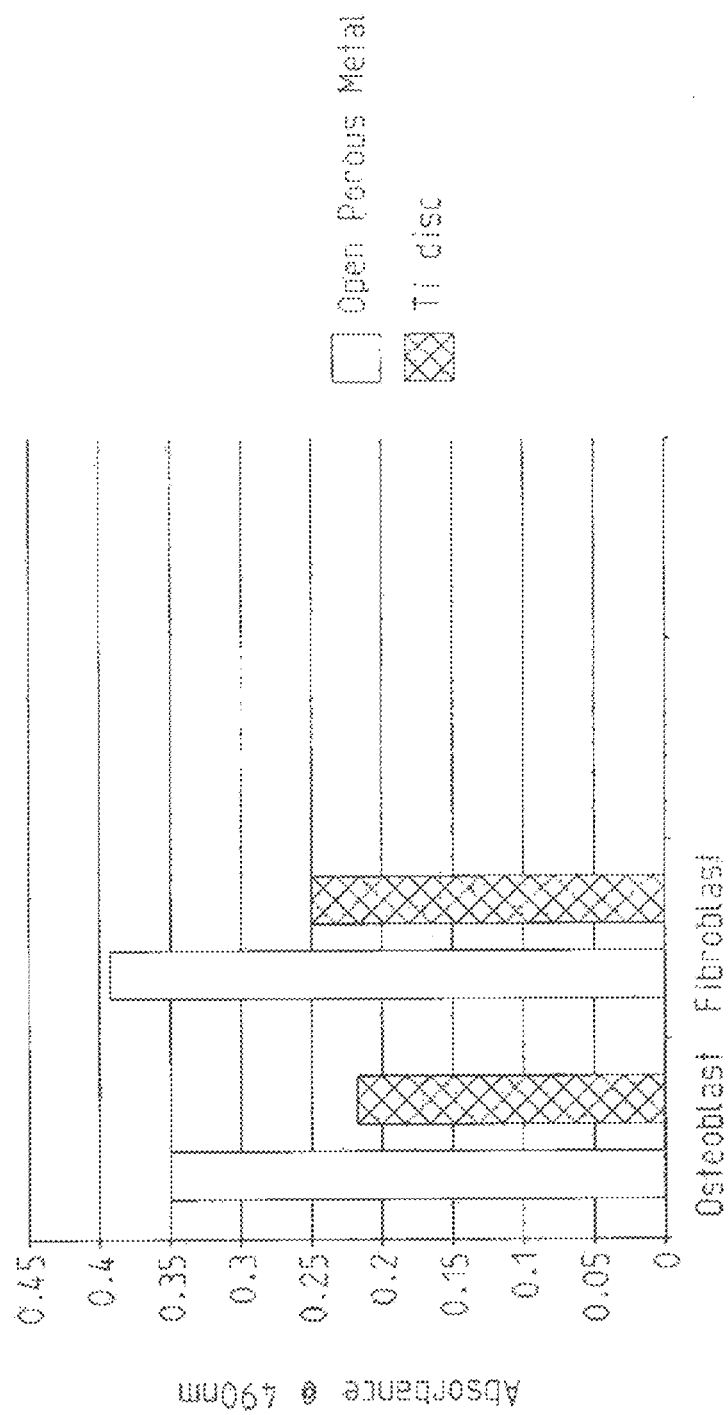
FIG. 10 presents two bar graphs illustrating osteoblast and fibroblast cell proliferation, respectively, on the porous tantalum disc utilized in the Examples disclosed herein, compared to the control titanium disc.

Referring to FIG. 10, quantitative measurement of cell proliferation by nonradioactive cell proliferation (MTS) assay from Promega, after ten days of culture, is shown. As shown, cell proliferation (of both osteoblasts and fibroblasts) on the porous tantalum discs was significantly greater than on the control titanium discs.

Figure 11:
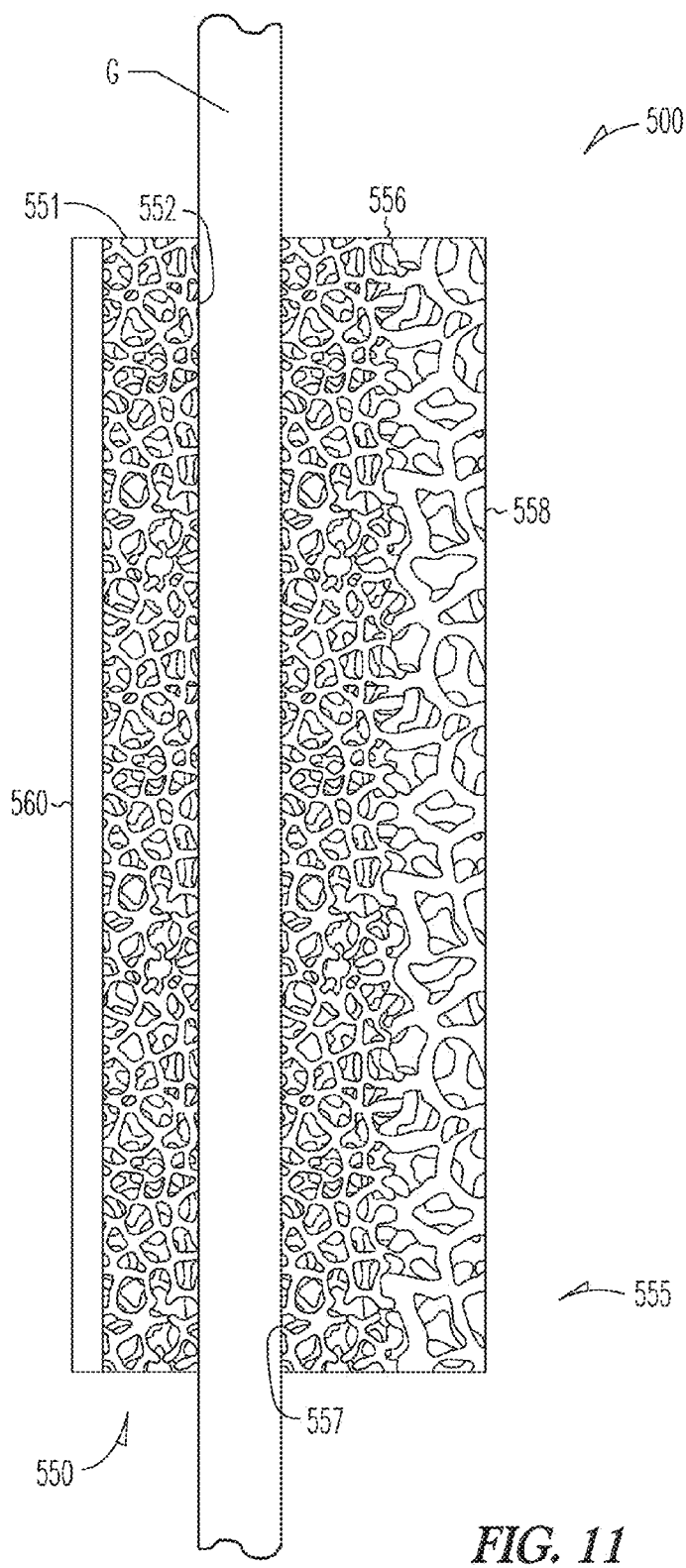
FIG. 11 is a side view of an orthopaedic implant according to one embodiment of the present disclosure with soft tissue of a patient positioned in the implant.

With reference now to FIG. 11, shown is another implant system 500 of the present disclosure that locates open porous metal components with different characteristics, e.g., pore sizes and porosities, at different regions or surfaces of the system. This illustrative system includes a first element 550 and a second element 555. First element 550 includes a first open porous metal structure 551 having a first exposed porous surface region 552 that is particularly adapted for contacting soft tissue or a soft tissue graft G. Second element 555 includes a second open porous metal structure 556 that can mimic one or more of the features described above in relation to structure 100a of FIG. 2a. For example, as illustrated, second open porous metal structure 556 provides a second exposed porous surface region 557 that is particularly adapted for contacting soft tissue or a soft tissue graft G and a third exposed porous surface region 558 that is adapted for contacting bone (not shown). In this regard, the nominal pore size of the second open porous metal structure 556 can be relatively greater in third exposed porous surface region 558 than in second exposed porous surface region 557 and first exposed porous surface region 552. Alternatively, structure 556 could be configured with an interface substrate or layer similar to that shown in element 100b of FIG. 2b. Additionally, system 500 includes an optional outermost coating or layer 560 (e.g., a pure titanium plate) that is essentially non-porous or measurably less porous than first structure 551, for example, to inhibit cellular invasion and ingrowth thereon and/or to protect surrounding tissues that might contact the layer following implantation. In some preferred forms, layer 560 is bonded or otherwise connected to first structure 551, or it is integrally formed into structure 551.

Continuing with FIG. 11, first structure 551 and second structure 556 can each be shaped and configured in a variety of manners, for example, as a sheet, layer, disc, planar or non-planar plate (e.g., with curvature), or any other suitable three-dimensional shape. Such structures can be particularly adapted for interacting with a tendon or other tissue G, for example, where a channel, passage or other space is provided in one or both of the structures for receiving at least part of the tissue or graft. In some preferred forms, first structure 551 and second structure 556 both form part of a single or monolithic piece of porous metal that is adapted to receive tissue G in or through the monolithic piece. In some other preferred forms, first structure 551 and second structure 556 are initially distinct and separate pieces (e.g., solid discs or washers) that are later arranged together in the assembly of system 500. Optionally, these separate pieces can be designed to cooperatively fit together, for example, where the pieces contact one another around the soft tissue or soft tissue graft G to fully or partially enclose portions of the graft. When system components such as first structure 551 and second structure 556 are initially separate pieces, they can be held together in any suitable manner. Also in this regard, the system or any individual part within the system can be connected to the soft tissue G and/or to a bone in any suitable manner including by bonding and/or utilizing any usable one- or multiple-piece connection mechanism. For example, in one illustrative embodiment, one or more screws are inserted through layer 560 toward a bone so that the screw(s) pass through first structure 551 and second structure 556 (and optionally also through a tendon, ligament, etc.) before entering the bone for securing the soft tissue within the system and securing the system to the bone.

Figure 12A:
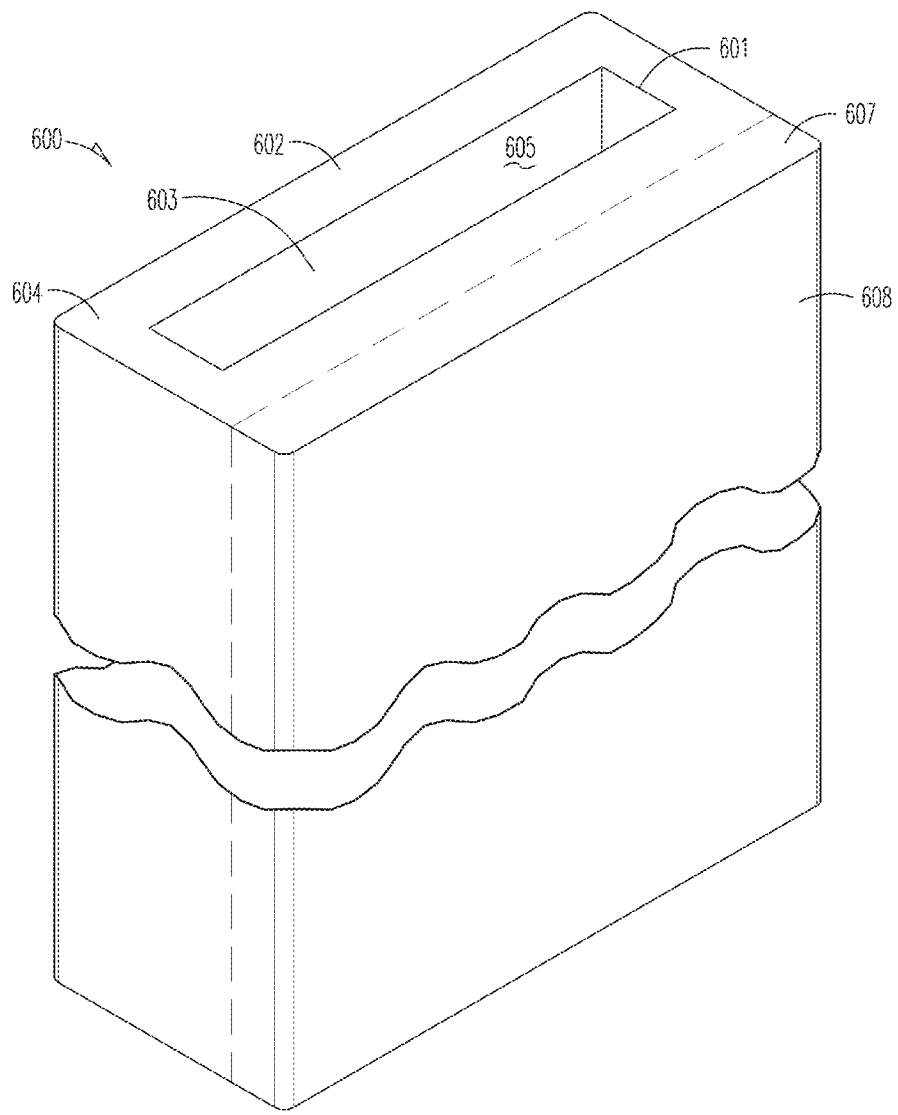
FIG. 12a is a perspective view of an orthopaedic implant according to another embodiment of the present disclosure.

FIG. 12A shows a generally rectangular parallelepiped open porous metal structure 600 according to one embodiment of the present disclosure. Structure 600 includes an opening 601 in a first end 602 of the structure that leads to an interior region 603 of the structure. In some aspects, structure 600 can mimic one or more of the features described above in relation to structure 100a of FIG. 2a. For example, as illustrated, a relatively lower porosity region 604 of the structure provides exposed interior porous surface walls 605 that are adjacent interior region 603 and that are particularly adapted for contacting soft tissue or a soft tissue graft, e.g., by inserting soft tissue into interior region 603 through opening 601 during a surgical procedure. A relatively higher porosity region 607 of the structure provides an exposed exterior porous surface wall 608 that is particularly adapted for contacting bone. In this regard, the nominal pore size is relatively greater in exposed exterior porous surface wall 608 than in exposed interior porous surface walls 605.

Figure 12B:
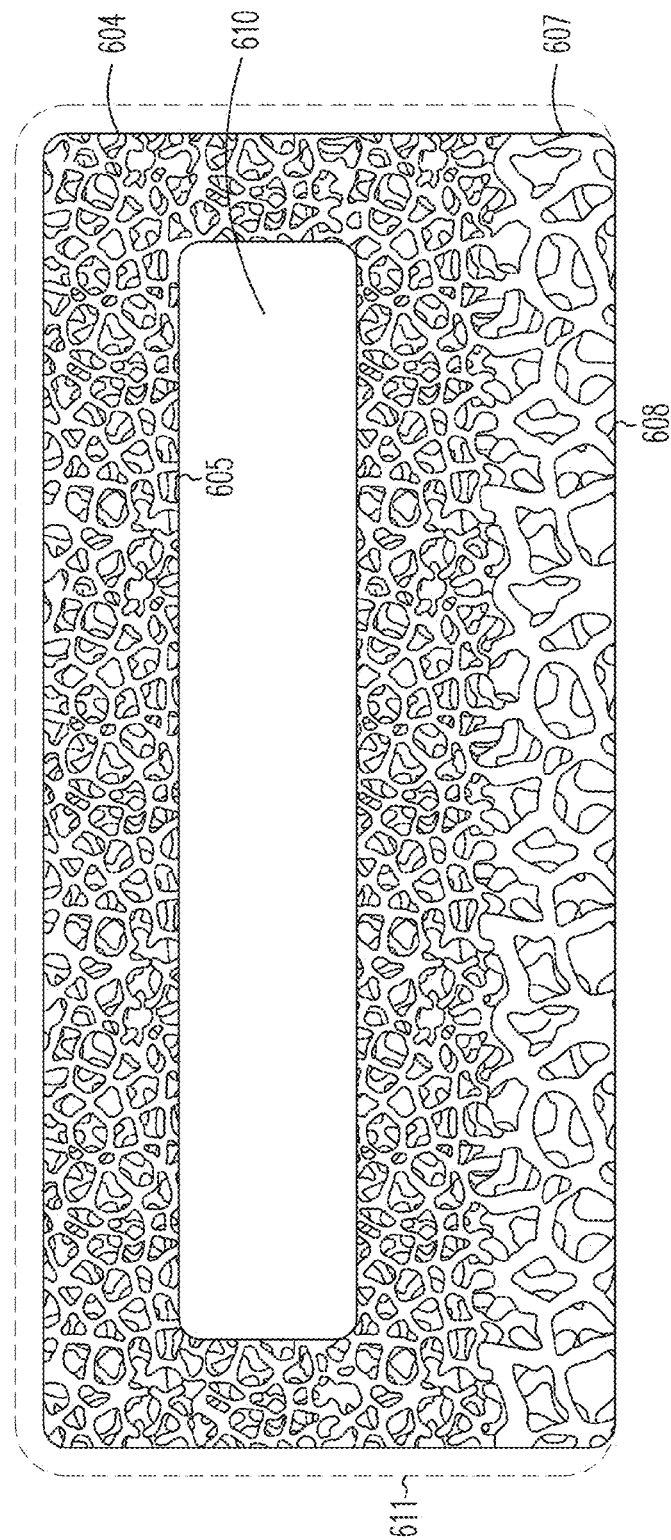

FIG. 12B shows an embodiment of structure 600 in which inferior region 603 provides a passage 610 extending fully through the structure from first opening 601 to a second opening in an opposite end of the structure. Such openings, interior regions, and passages can possess any suitable size and shape, and even the structure itself can be any suitable three-dimensional shape exhibiting rectilinear and/or curvilinear features. Also, an optional coating or layer 611 as shown on structure 600 in FIG. 12B is designed to inhibit cellular growth on the structure. Such a coating or layer can be placed on select surfaces of structure 600 such as walls or regions in which cellular ingrowth or ongrowth is not desired. In any suitable order, soft tissue can be secured in inferior region 603 and in contact with exposed interior porous surface walls 605, and exposed exterior porous surface wall 608 can be secured against bone. In doing so, the structure 600 can be attached to the soft tissue and the bone in any suitable manner including by bonding and/or utilizing any suitable one- or multiple-piece connection mechanism. In one preferred method, a recess or indentation will be made in the bone for receiving and containing all or part of relatively higher porosity region 607.

What is claimed is:

1. An implant for securing soft tissue to bone, comprising:
a tubular body providing an inner passageway for receiving soft tissue of a patient, wherein said inner passageway includes an interior side wall provided by a tubular first open porous metal structure with pores of a first nominal pore diameter for suitably receiving soft tissue ingrowth, said tubular body including an exterior side wall provided by a plate-shaped second open porous metal structure with pores of a second nominal pore diameter greater than said first nominal pore diameter for suitably receiving bone ingrowth, wherein said plate-shaped second open porous metal structure is located to a side of said tubular first open porous metal structure along a length of said tubular first open porous metal structure such that said inner passageway does not pass through said plate-shaped second open porous metal structure.

2. The implant of claim 1, wherein said tubular first open porous metal structure includes an inner passageway corresponding to the inner passageway of said tubular body.

3. The implant of claim 2, wherein said second open porous metal structure is non-tubular.

4. The implant of claim 1, wherein said tubular body includes a side wall thickness extending between the interior side wall of the inner passageway and the exterior side wall of the tubular body, said thickness provided entirely by open porous metal.

5. The implant of claim 1, wherein said first open porous metal structure extends around a full circumference of the inner passageway.

6. The implant of claim 1, wherein said tubular body includes a second exterior side wall that is essentially non-porous.

7. The implant of claim 1, wherein said first open porous metal structure and said second open porous metal structure are provided by a monolithic implant piece.

8. The implant of claim 3, wherein said monolithic implant piece incorporates a non-porous exterior layer providing a second exterior side wall of the tubular body.

9. The implant of claim 1, wherein the tubular body includes an exposed side exterior which includes the exterior side wall provided by the second open porous metal structure, and wherein the exterior side wall provided by the second open porous metal structure forms only part of said exposed side exterior.

10. The implant of claim 9, wherein said exposed side exterior includes a second exterior side wall provided by said first open porous metal structure.

11. The implant of claim 10, wherein said first open porous metal structure extends around a full circumference of the inner passageway.

12. The implant of claim 9, wherein said exposed side exterior includes a second exterior side wall provided by a non-porous coating or layer.

13. The implant of claim 12, wherein said first open porous metal structure extends around a full circumference of the inner passageway.

14. The implant of claim 9, wherein said tubular body is a monolithically-formed body.

15. The implant of claim 1, wherein said tubular body is a monolithically-formed body and includes an exposed side exterior which includes the exterior side wall provided by the second open porous metal structure, and wherein the exterior side wall provided by the second open porous metal structure forms only part of said exposed side exterior, the exposed side exterior including a second exterior side wall provided by an integrally-formed non-porous layer.

16. The implant of claim 1, wherein said tubular body includes a second exterior side wall provided by said first open porous metal structure such that said first open porous metal structure extends from said second exterior side wall to said interior side wall.

17. The implant of claim 2, wherein said exterior side wall that is provided by the second open porous metal structure is a first exterior side wall of the tubular body, and wherein said tubular first open porous metal structure provides a second exterior side wall of the tubular body.

18. An implant for securing soft tissue to bone, comprising:
a tubular body providing an inner passageway for receiving soft tissue of a patient, wherein said inner passageway includes an interior side wall provided by a tubular first open porous metal structure with pores of a first nominal pore diameter for suitably receiving soft tissue ingrowth, said tubular body including a first exterior side wall provided by a plate-shaped second open porous metal structure with pores of a second nominal pore diameter greater than said first nominal pore diameter for suitably receiving bone ingrowth, wherein said plate-shaped second open porous metal structure is located to a side of said tubular first open porous metal structure along a length of said tubular first open porous metal structure such that said inner passageway does not pass through said plate-shaped second open porous metal structure, said tubular body including a second exterior side wall that is less porous than said first open porous metal structure, said second exterior side wall being essentially non-porous.

19. The implant of claim 18, wherein said second exterior side wall is provided by a non-porous exterior layer integrally formed into said first open porous metal structure.

20. The implant of claim 19, wherein said first open porous metal structure and said second open porous metal structure are provided by a monolithic implant piece.

21. The implant of claim 18, wherein said exterior side wall that is provided by the second open porous metal structure is a first exterior side wall of the tubular body, and wherein said tubular first open porous metal structure provides a second exterior side wall of the tubular body, and wherein said tubular first open porous metal structure includes an inner passageway corresponding to the inner passageway of said tubular body.

22. An implant for securing soft tissue to bone, comprising:
a tubular body providing an inner passageway for receiving soft tissue of a patient, wherein said inner passageway includes an interior side wall provided by a tubular first open porous metal structure with pores of a first nominal pore diameter for suitably receiving soft tissue ingrowth, said tubular body including a first exterior side wall provided by a plate-shaped second open porous metal structure with pores of a second nominal pore diameter greater than said first nominal pore diameter for suitably receiving bone ingrowth, wherein said plate-shaped second open porous metal structure is located to a side of said tubular first open porous metal structure along a length of said tubular first open porous metal structure such that said inner passageway does not pass through said plate-shaped second open porous metal structure, said tubular body including a second exterior side wall provided by said first open porous metal structure such that said first open porous metal structure extends from said second exterior side wall to said interior side wall.

23. The implant of claim 22, wherein said first open porous metal structure extends around a full circumference of the inner passageway.

24. The implant of claim 23, wherein said first open porous metal structure and said second open porous metal structure are provided by a monolithic implant piece.

25. The implant of claim 22, wherein said tubular first open porous metal structure includes an inner passageway corresponding to the inner passageway of said tubular body.

26. An implant for securing soft tissue to bone, comprising:
an implant body including a tubular first open porous metal structure providing an inner passageway for receiving soft tissue of a patient, said inner passageway including an interior side wall with pores of a first nominal pore diameter for suitably receiving soft tissue ingrowth, said implant body further including a plate-shaped second open porous metal structure providing an exterior side wall of the implant body, said exterior side wall having pores of a second nominal pore diameter greater than said first nominal pore diameter for suitably receiving bone ingrowth, wherein said plate-shaped second open porous metal structure is located to a side of said tubular first open porous metal structure along a length of said tubular first open porous metal structure such that said inner passageway does not pass through said plate-shaped second open porous metal structure.

27. The implant of claim 26, wherein said tubular first open porous metal structure and said plate-shaped second open porous metal structure are provided by a monolithic implant piece.

* * * * *

UNITED STATES PATENT AND TRADEMARK OFFICE
CERTIFICATE OF CORRECTION

| | | |
|---|---|---|
| PATENT NO. | : 9,055,977 B2 | Page 1 of 1 |
| APPLICATION NO. | : 13/679041 | |
| DATED | : June 16, 2015 | |
| INVENTOR(S) | : Jiang et al. | |

It is certified that error appears in the above-identified patent and that said Letters Patent is hereby corrected as shown below:

In the claims
In column 20, line 20, in Claim 8, delete "claim 3," and insert --claim 7,--, therefor Signed and Sealed this
Twenty-ninth Day of December, 2015

Michelle K. Lee
*Director of the United States Patent and Trademark Office*